US009464310B2

(12) United States Patent
Adelson et al.

(10) Patent No.: US 9,464,310 B2
(45) Date of Patent: Oct. 11, 2016

(54) INTEGRATED METHOD FOR COLLECTION AND MAINTENANCE OF DETECTABILITY OF A PLURALITY OF MICROBIOLOGICAL AGENTS IN A SINGLE CLINICAL SAMPLE AND FOR HANDLING A PLURALITY OF SAMPLES FOR REPORTING A SUM OF DIAGNOSTIC RESULTS FOR EACH SAMPLE

(75) Inventors: Martin E. Adelson, Hillsborough, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 1491 days.

(21) Appl. No.: 11/343,822

(22) Filed: Jan. 31, 2006

(65) Prior Publication Data

US 2007/0042355 A1 Feb. 22, 2007

Related U.S. Application Data

(60) Provisional application No. 60/651,688, filed on Feb. 10, 2005, provisional application No. 60/654,485, filed on Feb. 18, 2005, provisional application No. 60/654,729, filed on Feb. 18, 2005.

(51) Int. Cl.
*C12Q 1/04* (2006.01)
*G01N 33/569* (2006.01)
*G06F 19/00* (2011.01)

(52) U.S. Cl.
CPC ............... *C12Q 1/045* (2013.01); *C12Q 1/04* (2013.01); *G01N 33/569* (2013.01); *G06F 19/363* (2013.01)

(58) Field of Classification Search
USPC ............... 435/6.1, 6.11, 6.12, 29, 68.1, 91.2, 435/235.1, 325, 243
See application file for complete search history.

(56) References Cited

U.S. PATENT DOCUMENTS

| | | | |
|---|---|---|---|
| 5,843,667 A * | 12/1998 | Weisburg et al. | ................ 435/6 |
| 6,174,670 B1 | 1/2001 | Wittwer et al. | |
| 6,210,891 B1 | 4/2001 | Nyren et al. | |
| 6,241,980 B1 * | 6/2001 | Collis et al. | ............... 424/78.11 |
| 6,258,568 B1 | 7/2001 | Nyren | |
| 6,387,621 B1 | 5/2002 | Wittwer | |
| 6,691,041 B2 | 2/2004 | Sagner et al. | |
| 6,830,935 B1 * | 12/2004 | El-Amin et al. | ............... 436/177 |
| 2003/0104372 A1 | 6/2003 | Ahmadian et al. | |
| 2003/0124545 A1 | 7/2003 | Rothman et al. | |
| 2003/0165833 A1 | 9/2003 | Hogan et al. | |
| 2004/0153254 A1 | 8/2004 | Sagner et al. | |
| 2004/0235010 A1 | 11/2004 | Rothman et al. | |

OTHER PUBLICATIONS

Moberg et al. Real-time PCR-based system for simultaneous quantification of human papillomavirus types associated with a high risk of cervical cancer. Journal of Clinical Microbiology 41(7): 3221-3228 (2003).*
Elahi et al. Determination of hepatitis C virus genotype by pyrosequencing. Journal of Virological Methods 109(2): 171-176 (2003).*
Josephson, S.L. An update on the collection and transport of specimens for viral culture. Clinical Microbiology Newsletter 19(8): 57-61 (1997).*
Martin & Lester. Transgrow, a Medium for Transport and Growth of Neisseria gonorrhoeae and Neisseria meningitides. HSMHA Health Reports 86:30-33, Jan. 1971.*
Gygax et al., Erythromycin and clindamycin resistance in Group B Streptococcal clinical isolates. Presented by Dr. Martin E. Adelson at the 45th ICAAC (Interscience Conference on Antimicrobial Agents and Chemotherapy) Meeting in Washington DC on Dec. 16, 2005.
Adelson et al., Evaluation of UTM-RT for the molecular detection of a plurality of OB/GYN related pathogens. Presented by Dr. Martin E. Adelson at the 45th ICAAC (Interscience Conference on Antimicrobial Agents and Chemotherapy) Meeting in Washington DC on Dec. 17, 2005.
Gynecology Test Requisition Form, published by Medical Diagnostics Laboratories LLC between Nov. 15, 2004 and Jan. 31, 2005.
Adelson et al., U.S. Appl. No. 11/343,826, filed Jan. 31, 2006.
Adelson et al., U.S. Appl. No. 11/343,858, filed Jan. 31, 2006.
Trams et al. Analyzing Candida albicans gene mutations that contribute to azole resistance by pyrosequencing. American College of Obstetricians and Gynecologists 52nd Annual Clinical Meeting, May 1-5, 2004, Philadelphia, PA.
Trams et al. Novel technique for identification of vulvovaginal candidiasis by real-time PCR and pyrosequencing. American College of Obstetricians and Gynecologists 52nd Annual Clinical Meeting, May 1-5, 2004, Philadelphia, PA.
Adelson et al., Diagnosis of Neisseria gonorrhea, Chlamydia trachomatis, and Trichomonas vaginalis by real-time PCR, American College of Obstetricians and Gynecologists 52nd Annual Clinical Meeting, May 1-5, 2004, Philadelphia, PA.
Mordechai et al., Prevalency of Candida species associated with Candida vaginitis in the United States, American Society of Microbiology 104th General Meeting, May 23-27, 2004, New Orleans, LA, Poster C-108.
Adelson et al., Development of a real-time PCR assay for the simultaneous detection of herpes simplex virus types 1 and 2 with confirmation by pyrosequencing technology, American Society of Microbiology 104th General Meeting, May 23-27, 2004, New Orleans, LA, Poster C-273.
Naurath et al., Detection and quantification of Gardnerella vaginalis by real-time PCR, American College of Obstetricians and Gynecologists 53rd Annual Clinical Meeting, May 7-11, 2005, San Francisco, CA.
Trama et al, Detection of molluscum contagiosum virus by real-time PCR and pyrosequencing, American Society of Microbiology 105th General Meeting, Jun. 5-9, 2005, Atlanta, GA.

(Continued)

*Primary Examiner* — Samuel Woolwine
(74) *Attorney, Agent, or Firm* — Siu K. Lu

(57) ABSTRACT

A method and kit related thereto are described for the collection and maintenance of detectability of a plurality of species of microbiological agents in a single clinical sample as well as an integral method for handling a plurality of the samples and managing information associated therewith for reporting a sum of diagnostic results for each sample.

16 Claims, 14 Drawing Sheets

(56) References Cited

OTHER PUBLICATIONS

Feola et al., Detection of Ureaplasma urealyticum, Mycoplasma hominis; and Mycoplasma genitalium by real-time PCR and pyrosequencing, American Society of Microbiology 105th General Meeting, Jun. 5-9, 2005, Atlanta, GA.

Trama et al., 2005, Detection of Candida species in vaginal samples in a clinical laboratory setting. Infectious Diseases in Obstetrics and Gynecology 13(2):63-67.

Ronaghi et al., 1998, A sequencing method based on real-time pyrophosphate. Science 281:363, 365.

Ronaghi, 2001, Pyrosequencing sheds light on DNA sequencing. Genome Research 11:3-11.

Adelson et al., 2005, Simultaneous detection of herpes simplex virus types 1 and 2 by real-time PCR and pyrosequencing. Journal of Clinical Virology 33:25-34. (manuscript published online on Nov. 14, 2004).

Trama et al., 2005, Detection and identification of Candida species associated with Candida vaginitis by real-time PCR and pyrosequencing. Molecular and Cellular Probes 19(2):145-152.

Goessens et al., 1995, Influence of volume of sample processed on detection of Chlamydia trachomatis in urogenital samples by PCR. Journal of Clinical Microbiology 33:251-253.

Goessens et al. 1997, Comparison of three commercially available amplification assays, AMP CT, LCx, and COBAS Amplicor, for detection of Chlamydia trachomatis in first-void urine. 35(10):2628-2633.

Van Doornum et al, 2001, Comparison between the LCx probe system and the Cobas Amplicor system for detection of Chlamydia trachomatis and Neisseria gonorrhoeae infections in patients attending a clinic for treatment of sexually transmitted diseases in Amsterdam, The Netherlands. Journal of Clinical Microbiology 39(3):829-835.

Gynecology Test Requisition Form, published by Medical Diagnostics Laboratories LLC before Feb. 10, 2004.

PCR testing for best results recommended specimen collection procedures, published by Medical Diagnostic Laboratories LLC before Feb. 10, 2004.

Description of BD Cellmatics Viral Transport Pack, May 2002, Publication No. S1059JAA, Becton, Dickinson and Company, Sparks, MD.

Description of BD Cellmatics Viral Transport Pack, Oct. 2001, Publication No. 0-2528, Becton, Dickinson and Company, Sparks, MD.

Test Requisition Form, published by Medical Diagnostics Laboratories LLC before Feb. 10, 2004.

Sotlar et al., 2004. Detection and typing of human papillomavirus by E6 nested multiplex PCR. Journal of Clinical Microbiology 42:3176-3184.

Non-Final Office Action mailed Jun. 2, 2014, for U.S. Appl. No. 11/343,858, filed Jan. 31, 2006.

Non-Final Office Action mailed May 12, 2014 for U.S. Appl. No. 11/343,826, filed Jan. 31, 2006.

\* cited by examiner

Figure 1
Gynecology Test Requisition Form

| Patient Information (Please Print): | | | Ordering Physician/Laboratory | | |
|---|---|---|---|---|---|
| Name (Last, First): | | | Physician's Name: | | UPIN #: |
| In Care of: | | | Address: | | |
| Patient Address: | | | 2nd Address: | | |
| City: | State: | Zip Code: | City: | State: | Zip: |
| ☐ Female ☐ Male | Date of Birth (Required): | | Phone Number: | | Fax Number: |
| Patient SSN: | | Patient ID #: | Physician's Signature: | | Date: |
| Phone Number (9 am to 5 pm): | | | Physician to receive additional result report. | | |
| Billing Information (Please include a copy of the front & back of card if available) | | | | | |
| ☐ Patient Billing<br>☐ Insurance Billing<br>☐ Lab Account<br>☐ Physician Account | Relation:<br>☐ Spouse<br>☐ Self<br>☐ Dependant | | ICD9 Codes (Required): Please provide all diagnosis codes applicable for tests medically necessary for the diagnosis and treatment of the patient. | | |
| Primary Insurance Carrier: | | | Claims Address: | | |
| Medicare ID # or Medicaid ID #: | | | Policy ID #: | Group #: | |
| Specimen Information | | | | | |
| Date Collected (Required): | | | Specimen Source: | Comments: | |

☐ *Bacteroides fragilis*
☐ *Candida albicans*
☐ *Candida glabrata*
☐ *Candida parapsilosis*
☐ *Candida tropicalis*
☐ *Chlamydia trachomatis*
☐ *Gardnerella vaginalis*
☐ *Haemophilus ducreyi*
☐ Herpes subtype (HSV-1, HSV-2)
☐ Herpes simplex virus (HSV) viral load
☐ HPV subtyping (High/Low Risk of Cervical Cancer)
☐ *Mobiluncus mulieris* and *M. curtisii*
☐ Molluscum contagiosum virus
☐ *Mycoplasma genitalium*
☐ *Mycoplasma hominis*
☐ *Neisseria gonorrhoeae*
☐ *Treponema pallidum* (syphilis)
☐ *Trichomonas vaginalis*
☐ *Ureaplasma urealyticum*
☐ Vaginal Group B Strep (GBS)
☐ Bacterial Vaginosis Panel (*Mobiluncus mulieris, M. curtisii, Bacteroides fragilis, Gardnerella vaginalis*
☐ Candida Vaginitis Panel (*Candida albicans, Candida glabrata, Candida parapsilosis, Candida tropicalis*)
☐ Genital Ulcer Disease Panel (HSV-1, HSV-2, *T. pallidum* (syphilis), *H. ducreyi)*
☐ Leukorrhea Panel (*N. gonorrhoeae, C. trachomatis, T. vaginalis*)

Figure 4
| Days | Copy number | Ct value |
|---|---|---|
| 0 | 1.90E+07 | 19.85 |
| 0 | 2.13E+07 | 19.67 |
| 0 | 1.66E+07 | 20.06 |
| 1 | 2.02E+07 | 19.76 |
| 1 | 2.44E+07 | 19.46 |
| 1 | 1.52E+07 | 20.2 |
| 2 | 1.33E+06 | 23.96 |
| 2 | 6.36E+06 | 21.54 |
| 2 | 7.28E+06 | 21.33 |
| 3 | 8.90E+06 | 21.02 |
| 3 | 2.40E+07 | 19.49 |
| 3 | 1.58E+07 | 20.14 |
| 4 | 1.16E+07 | 20.61 |
| 4 | 4.61E+06 | 22.04 |
| 4 | 2.13E+07 | 19.68 |
| 5 | 3.55E+07 | 18.88 |
| 5 | 7.53E+07 | 17.72 |
| 5 | 4.79E+07 | 18.42 |
| 5000000 | 5.00E+06 | 17.7 |
| 5.E+04 | 5.00E+04 | 24.81 |
| 5.E+02 | 5.00E+02 | 31.92 |
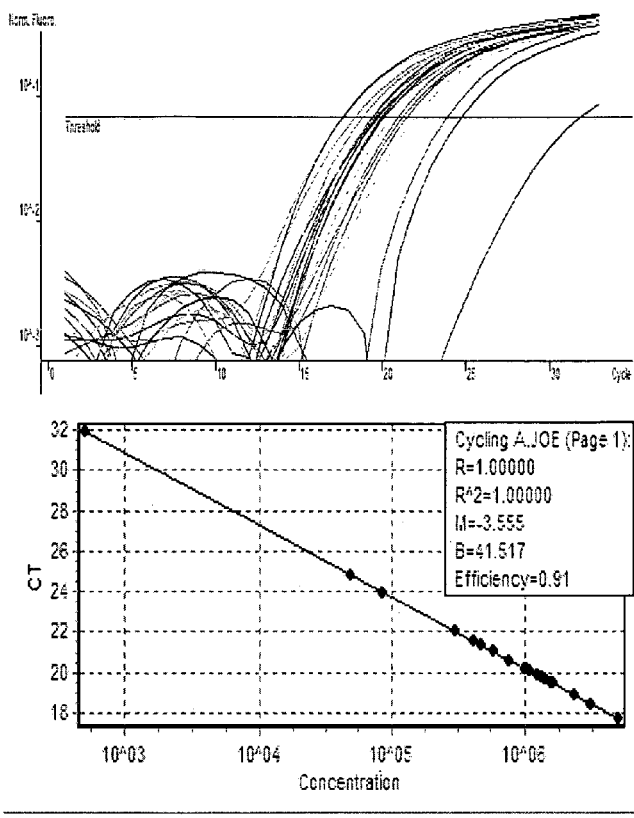
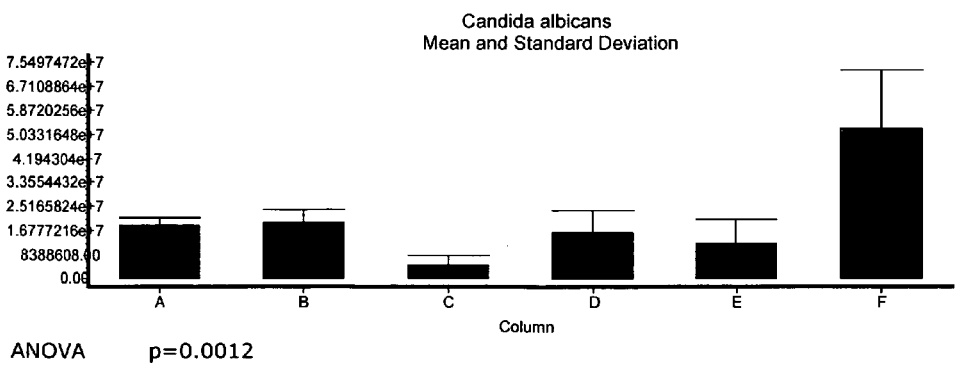
Candida albicans
Mean and Standard Deviation
ANOVA    p=0.0012

Figure 5
*Candida glabrata*
| Days | Copy number | Ct value |
|---|---|---|
| 0 | 9.39E+06 | 17.75 |
| 0 | 1.46E+07 | 16.98 |
| 0 | 2.03E+07 | 16.41 |
| 1 | 1.10E+07 | 17.48 |
| 1 | 5.48E+05 | 22.69 |
| 1 | 7.90E+06 | 18.05 |
| 2 | 0.00E+00 | 0 |
| 2 | 0.00E+00 | 0 |
| 2 | 1.29E+06 | 21.2 |
| 3 | 7.14E+05 | 22.23 |
| 3 | 4.23E+05 | 23.14 |
| 3 | 4.58E+05 | 23 |
| 4 | 2.34E+05 | 24.17 |
| 4 | 0.00E+00 | 0 |
| 4 | 0.00E+00 | 0 |
| 5 | 5.36E+07 | 14.72 |
| 5 | 2.03E+07 | 16.41 |
| 5 | 1.52E+06 | 20.92 |
| Std. 5000000 | 9.91E+05 | 16.92 |
| Std. 50000 | 3.29E+05 | 18.84 |
| Std. 500 | 3.84E+02 | 30.58 |
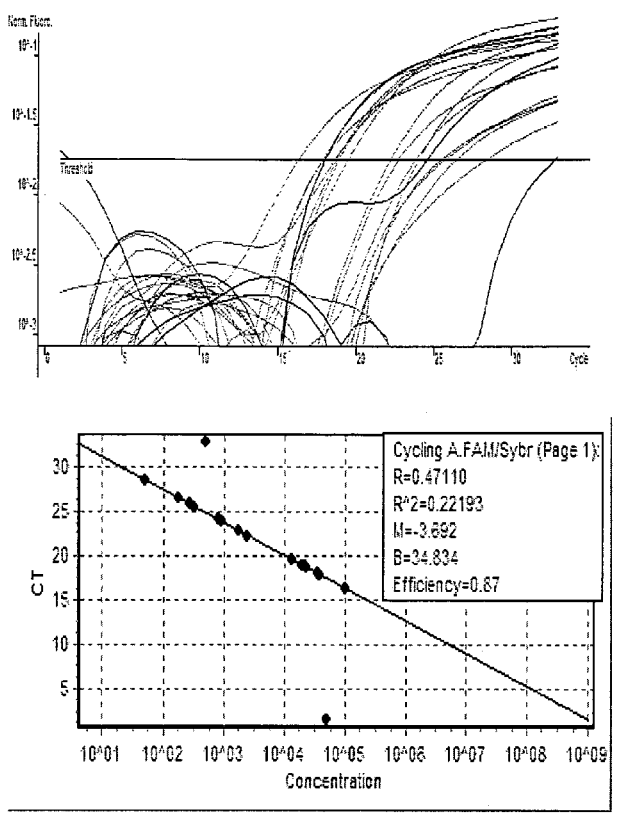
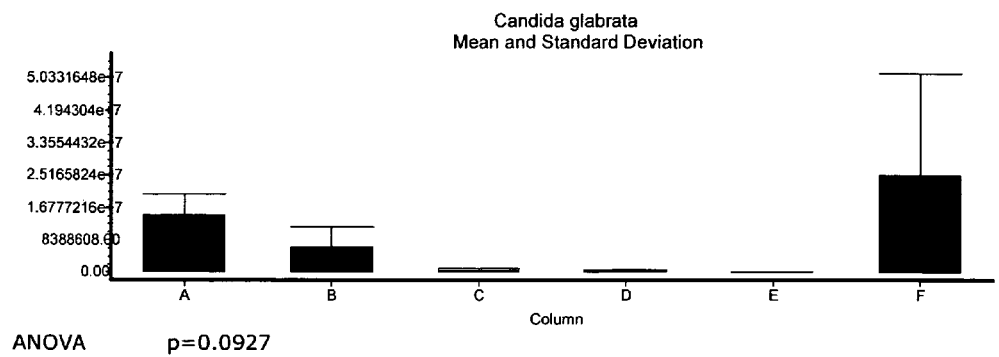
Candida glabrata
Mean and Standard Deviation
ANOVA    p=0.0927

Figure 6
*Candida parapsilosis*
| Days | Copy number | Ct value |
|---|---|---|
| 0 | 3.96E+05 | 23.24 |
| 0 | 1.15E+06 | 21.7 |
| 0 | 3.28E+06 | 20.2 |
| 1 | 9.16E+06 | 18.72 |
| 1 | 4.50E+06 | 19.74 |
| 1 | 5.06E+06 | 19.57 |
| 2 | 5.79E+06 | 19.38 |
| 2 | 3.92E+06 | 19.94 |
| 2 | 6.89E+05 | 22.44 |
| 3 | 0.00E+00 | 0 |
| 3 | 4.67E+06 | 19.69 |
| 3 | 8.87E+06 | 18.77 |
| 4 | 2.00E+07 | 17.6 |
| 4 | 1.53E+07 | 17.98 |
| 4 | 1.71E+07 | 17.82 |
| 5 | 5.66E+06 | 19.41 |
| 5 | 8.41E+06 | 18.84 |
| 5 | 1.20E+07 | 18.33 |
| Std. 5000000 | 5.00E+06 | 15.7 |
| Std. 50000 | 5.00E+04 | 22.23 |
| Std. 500 | 5.00E+02 | 29.95 |
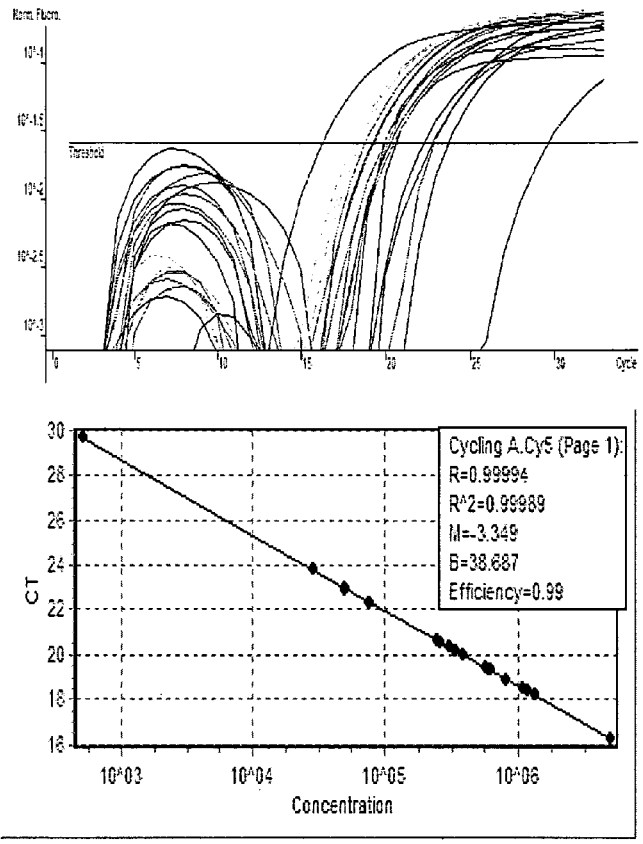
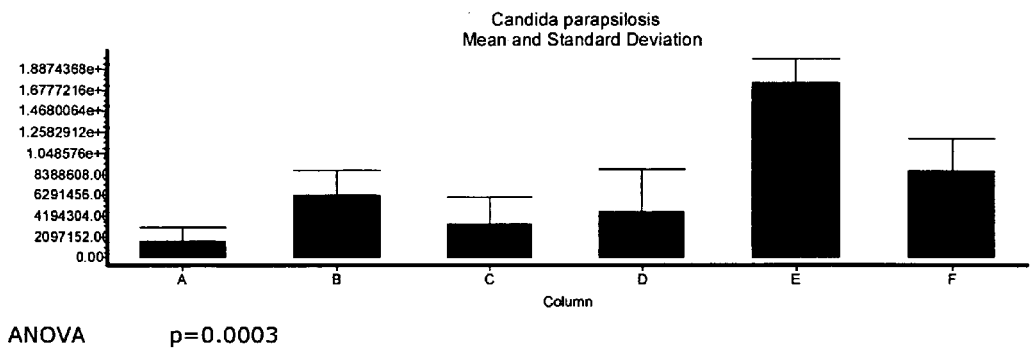
ANOVA    p=0.0003

Figure 7
*Candida tropicalis*
| Days | Copy number | Ct value |
|---|---|---|
| 0 | 3.11E+08 | 18.25 |
| 0 | 2.42E+08 | 18.63 |
| 0 | 2.39E+08 | 18.65 |
| 1 | 3.19E+08 | 18.21 |
| 1 | 1.95E+08 | 18.96 |
| 2 | 2.08E+08 | 18.86 |
| 2 | 2.86E+08 | 18.38 |
| 2 | 1.20E+08 | 19.68 |
| 3 | 2.17E+08 | 18.8 |
| 3 | 2.78E+08 | 18.42 |
| 3 | 3.50E+08 | 18.07 |
| 4 | 6.32E+08 | 17.17 |
| 4 | 3.81E+08 | 17.94 |
| 4 | 4.04E+08 | 17.85 |
| 5 | 2.97E+08 | 18.83 |
| 5 | 5.58E+08 | 17.36 |
| 5 | 2.57E+08 | 18.54 |
| Std. 5000000 | 5.86E+06 | 20.15 |
| Std. 50000 | 3.31E+04 | 28.04 |
| Std. 500 | 1.29E+03 | 32.99 |
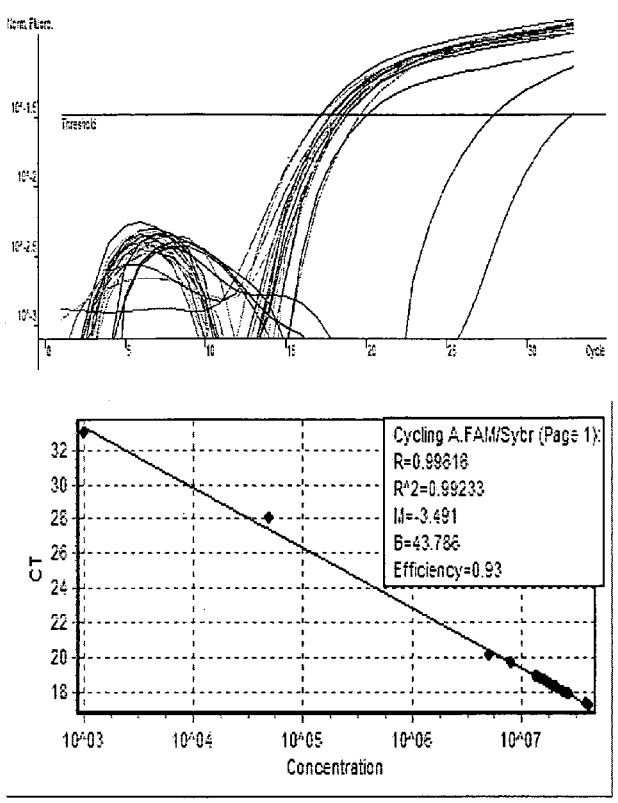
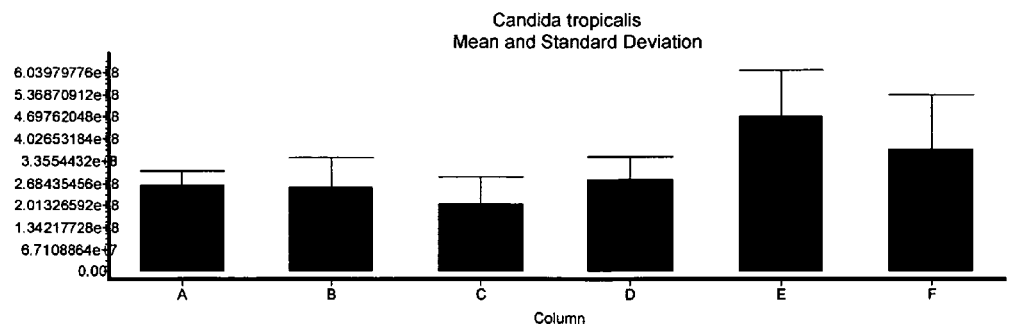
Candida tropicalis
Mean and Standard Deviation
ANOVA    p=0.1039

Figure 8
Chlamydia trachomatis
| Days | Copy number | Ct Value |
|---|---|---|
| 0 | 2.12E+08 | 15.68 |
| 0 | 3.23E+08 | 15.19 |
| 0 | 2.00E+08 | 15.74 |
| 1 | 8.15E+06 | 19.44 |
| 1 | 1.64E+07 | 18.63 |
| 1 | 5.58E+06 | 19.88 |
| 2 | 2.93E+06 | 20.63 |
| 2 | 3.80E+07 | 17.66 |
| 2 | 9.69E+06 | 19.24 |
| 3 | 1.85E+07 | 18.5 |
| 3 | 4.72E+07 | 17.41 |
| 3 | 2.16E+07 | 18.31 |
| 4 | 3.47E+07 | 17.77 |
| 4 | 1.88E+06 | 21.14 |
| 4 | 1.56E+09 | 13.37 |
| 5 | 1.82E+07 | 18.52 |
| 5 | 2.71E+08 | 15.39 |
| 5 | 1.40E+07 | 18.81 |
| Std. 500000 | 5.00E+05 | 19.67 |
| Std. 50000 | 5.00E+04 | 21.95 |
| Std. 500 | 5.00E+02 | 27.57 |
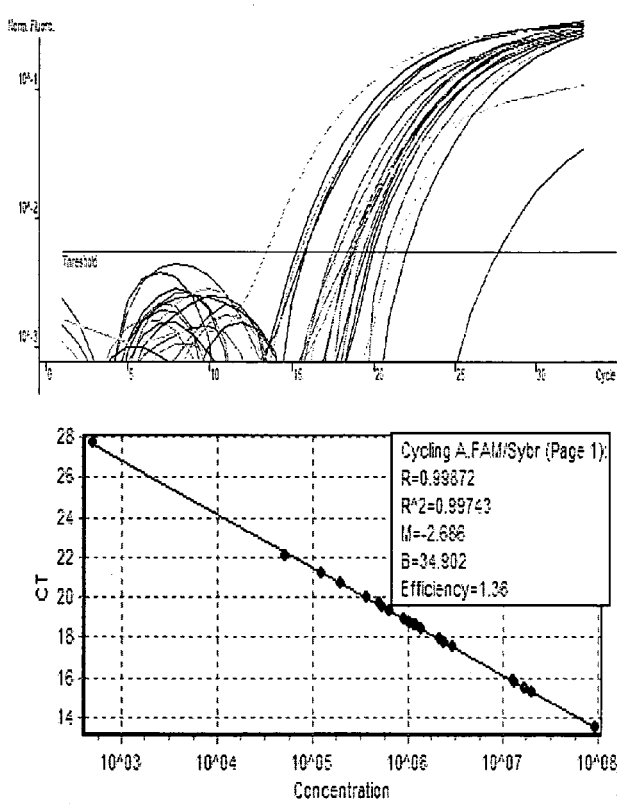
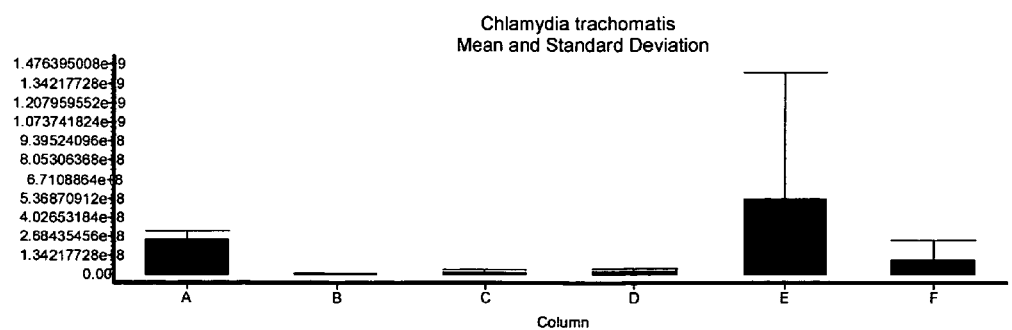
Chlamydia trachomatis
Mean and Standard Deviation
ANOVA    p=0.5011

Figure 9
*Gardnerella vaginalis*
| Days | Copy number | Ct value |
|---|---|---|
| 0 | 7.01E+07 | 21.13 |
| 0 | 5.43E+07 | 21.56 |
| 0 | 4.79E+07 | 21.77 |
| 1 | 6.08E+07 | 21.37 |
| 1 | 5.75E+07 | 21.46 |
| 1 | 4.94E+07 | 21.72 |
| 2 | 3.97E+07 | 22.09 |
| 2 | 3.65E+07 | 22.24 |
| 2 | 2.79E+07 | 22.69 |
| 3 | 4.37E+07 | 21.93 |
| 3 | 5.90E+07 | 21.42 |
| 3 | 3.24E+07 | 22.44 |
| 4 | 2.15E+07 | 23.13 |
| 4 | 2.03E+07 | 23.23 |
| 4 | 2.10E+07 | 23.18 |
| 5 | 3.43E+07 | 22.34 |
| 5 | 6.30E+07 | 21.31 |
| 5 | 3.06E+07 | 22.54 |
| 1:100 | 6.70E+06 | 20.3 |
| 1:1000 | 6.70E+05 | 24.76 |
| 1:10000 | 6.70E+04 | 28.14 |
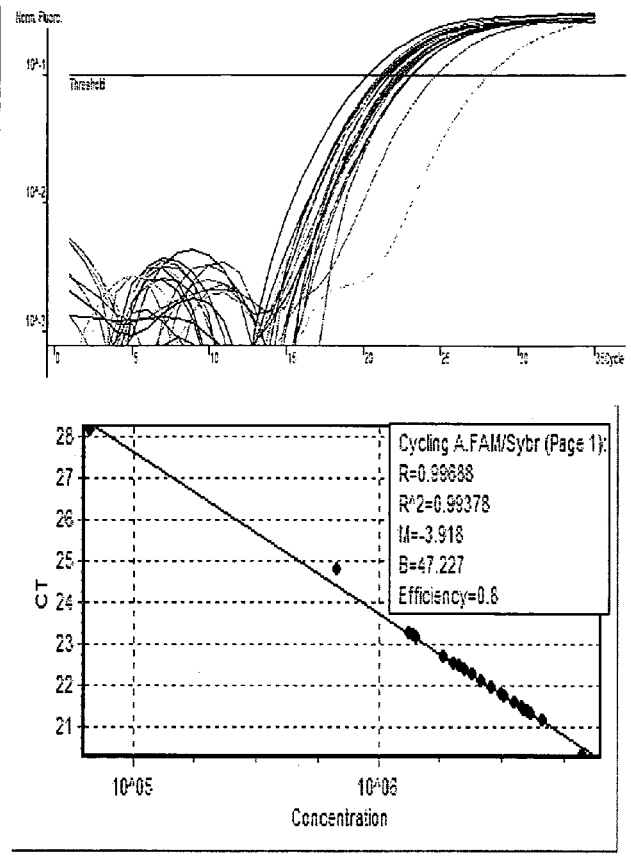
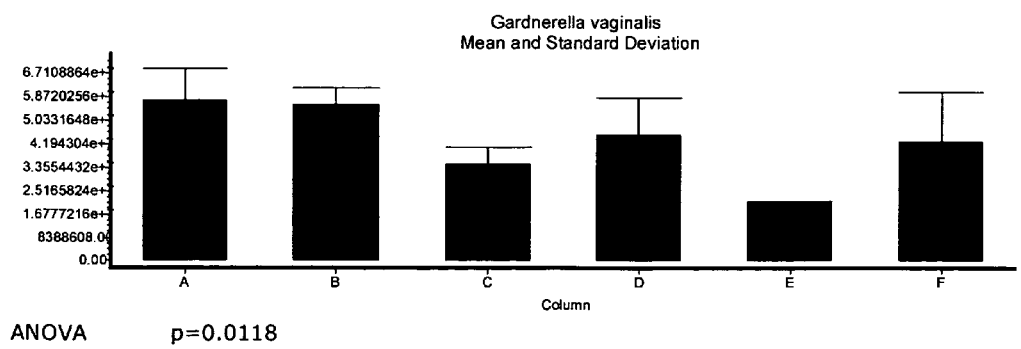
Gardnerella vaginalis
Mean and Standard Deviation
ANOVA    p=0.0118

Figure 10
*Haemophilis ducreyi*
| Days | Copy number | Ct value |
|---|---|---|
| 0 | 8.70E+05 | 19.8 |
| 0 | 6.70E+05 | 20.3 |
| 0 | 8.47E+05 | 19.85 |
| 1 | 5.30E+05 | 20.75 |
| 1 | 1.26E+06 | 19.09 |
| 1 | 6.10E+05 | 20.48 |
| 2 | 4.32E+03 | 29.98 |
| 2 | 8.92E+04 | 24.17 |
| 2 | 2.41E+05 | 22.26 |
| 3 | 8.21E+04 | 24.33 |
| 3 | 1.35E+05 | 23.37 |
| 3 | 4.33E+05 | 21.14 |
| 4 | 2.90E+05 | 21.91 |
| 4 | 1.14E+05 | 23.7 |
| 4 | 1.43E+05 | 23.27 |
| 5 | 9.45E+04 | 24.06 |
| 5 | 4.30E+05 | 21.15 |
| 5 | 3.66E+05 | 21.46 |
| Std. 10^7 | 1.00E+07 | 11.35 |
| Std. 10^5 | 1.00E+05 | 16.59 |
| Std. 10^3 | 1.00E+03 | 28.22 |
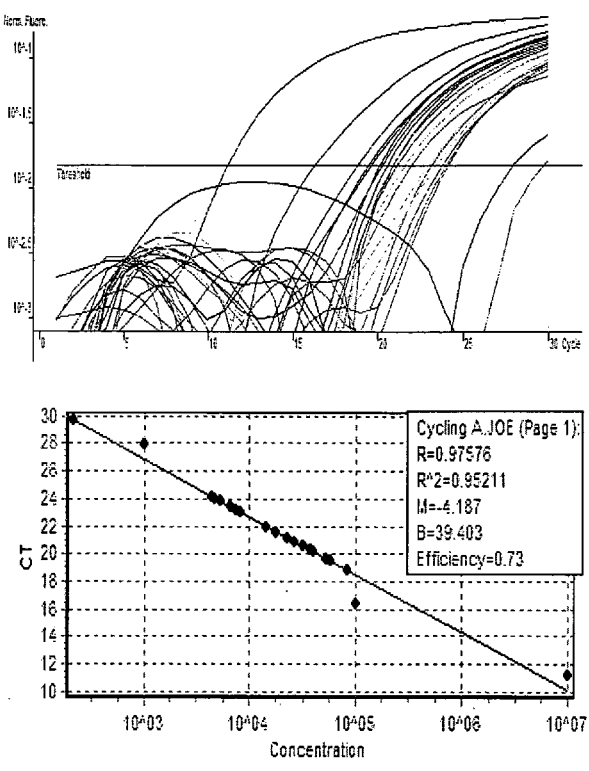
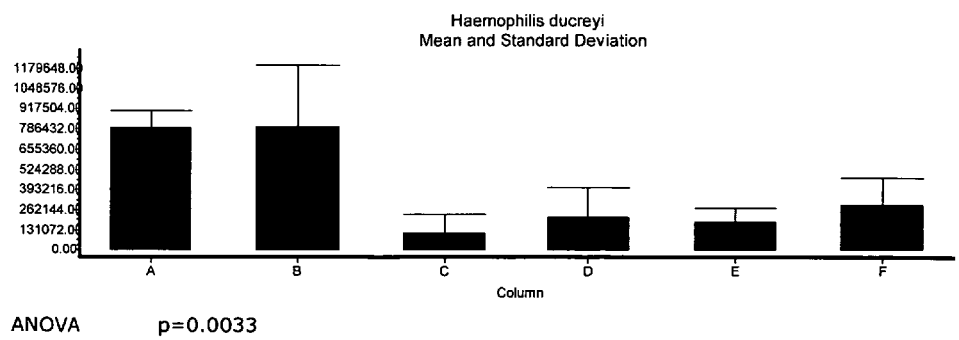
Haemophilis ducreyi
Mean and Standard Deviation
ANOVA    p=0.0033

Figure 11
HSV-1
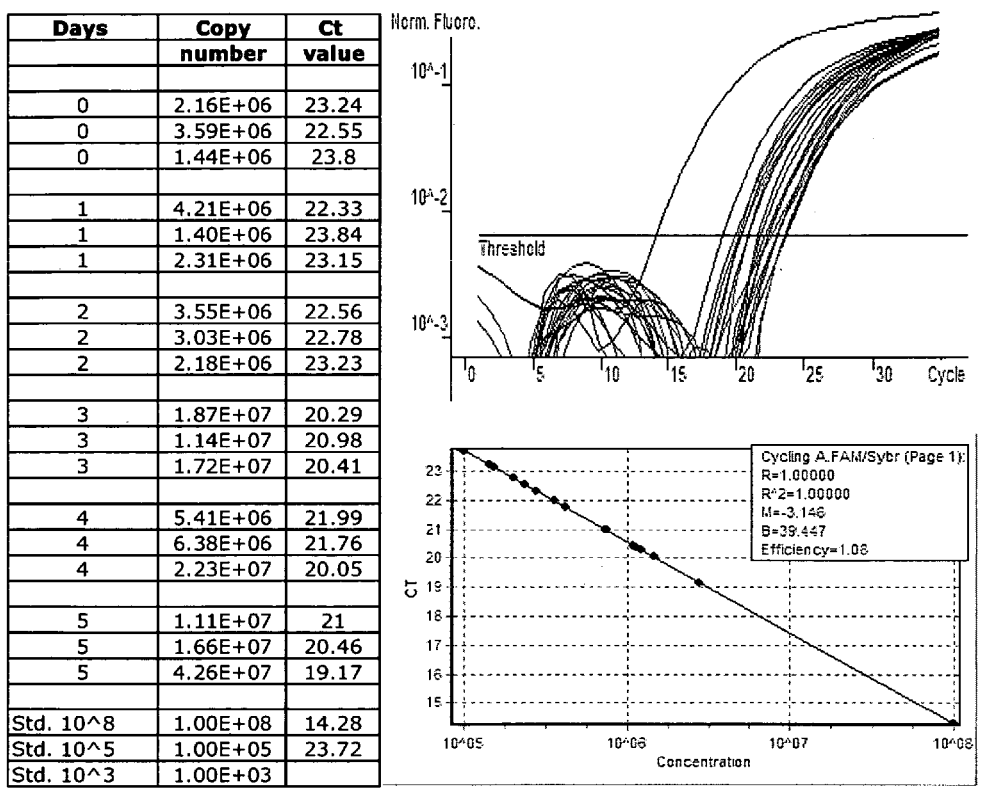
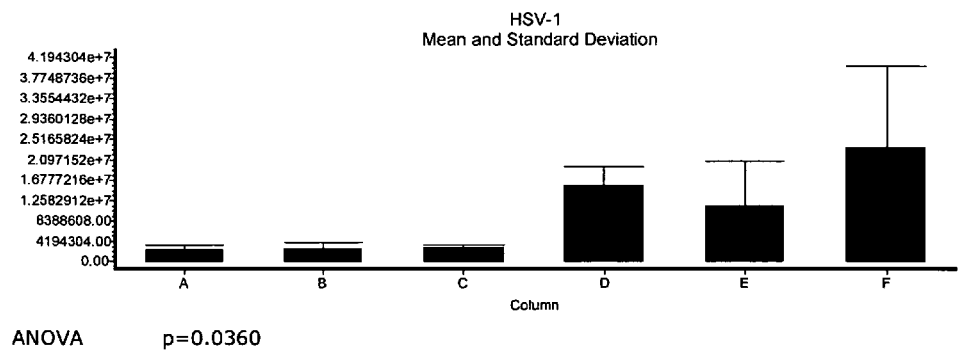
ANOVA    p=0.0360

Figure 12
HSV-2
| Days | Copy number | Ct value |
|---|---|---|
| 0 | 2.74E+09 | 12.21 |
| 0 | 3.54E+08 | 15.12 |
| 0 | 1.47E+09 | 13.1 |
| 1 | 6.57E+08 | 14.24 |
| 1 | 4.79E+08 | 14.69 |
| 1 | 6.26E+08 | 14.31 |
| 2 | 9.91E+08 | 13.67 |
| 2 | 8.47E+08 | 13.88 |
| 2 | 1.11E+09 | 13.5 |
| 3 | 6.76E+08 | 14.2 |
| 3 | 7.46E+08 | 14.06 |
| 3 | 8.00E+08 | 13.96 |
| 4 | 6.85E+08 | 14.18 |
| 4 | 8.19E+07 | 17.2 |
| 4 | 8.17E+08 | 13.93 |
| 5 | 8.53E+08 | 13.87 |
| 5 | 1.22E+09 | 13.36 |
| 5 | 6.62E+08 | 14.23 |
| Std. 10^8 | 1.00E+08 | 13.18 |
| Std. 10^5 | 1.00E+05 | 22.54 |
| Std. 10^3 | 1.00E+03 | 29.59 |
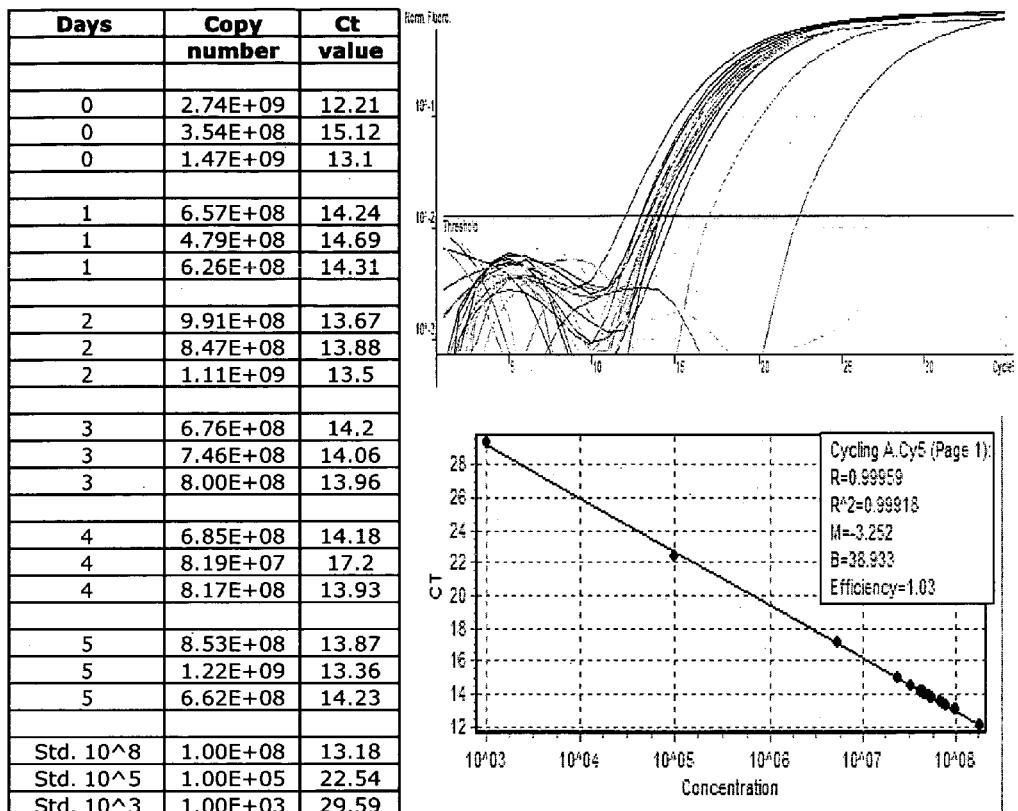
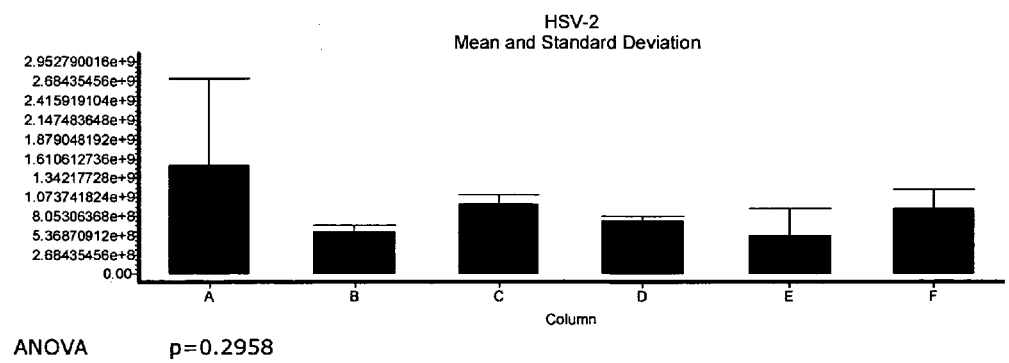
HSV-2
Mean and Standard Deviation
ANOVA    p=0.2958

Figure 13
*Trichomonas vaginalis*
| Days | Copy number | Ct value |
|---|---|---|
| 0 | 2.24E+05 | 29.64 |
| 0 | 6.12E+05 | 27.86 |
| 0 | 1.44E+05 | 30.42 |
| 1 | 1.73E+05 | 30.09 |
| 1 | 0.00E+00 | 0 |
| 1 | 2.71E+05 | 29.3 |
| 2 | 9.26E+04 | 31.2 |
| 2 | 8.39E+05 | 27.3 |
| 2 | 6.33E+05 | 27.8 |
| 3 | 7.01E+05 | 27.62 |
| 3 | 5.31E+05 | 28.11 |
| 3 | 5.62E+05 | 28.01 |
| 4 | 8.18E+04 | 31.42 |
| 4 | 6.52E+04 | 31.82 |
| 4 | 6.55E+05 | 27.74 |
| 5 | 1.03E+05 | 31.02 |
| 5 | 5.73E+04 | 32.05 |
| 5 | 3.42E+04 | 32.96 |
| Std. 10^6 | 1.00E+06 | 22.17 |
| Std. 10^5 | 1.00E+05 | 26.24 |
| Std. 10^3 | 1.00E+03 | 34.39 |
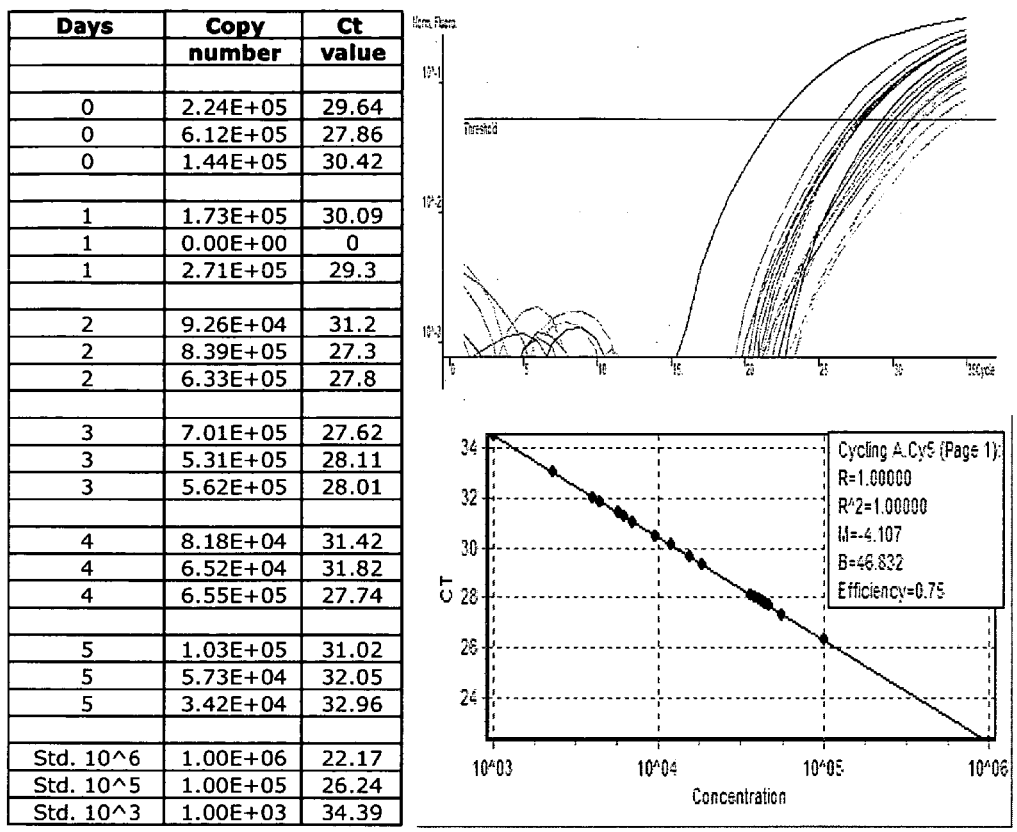
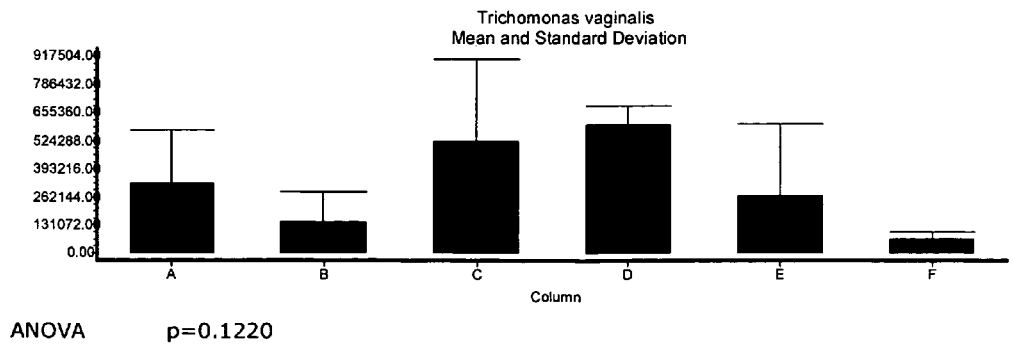
ANOVA   p=0.1220

Figure 14
*Ureaplasma urealyticum*
| Days | Copy number | Ct value |
|---|---|---|
| 0 | 2.05E+05 | 25.01 |
| 0 | 1.65E+05 | 25.49 |
| 0 | 2.70E+05 | 24.39 |
| 1 | 2.74E+05 | 24.36 |
| 1 | 2.36E+05 | 24.69 |
| 1 | 1.94E+05 | 25.13 |
| 2 | 3.21E+04 | 29.16 |
| 2 | 8.50E+04 | 29.98 |
| 2 | 6.27E+04 | 27.66 |
| 3 | 4.84E+04 | 28.24 |
| 3 | 9.25E+04 | 26.79 |
| 3 | 1.91E+05 | 25.16 |
| 4 | 3.61E+04 | 28.9 |
| 4 | 9.08E+04 | 26.83 |
| 4 | 8.80E+04 | 26.9 |
| 5 | 1.14E+05 | 26.32 |
| 5 | 1.26E+05 | 26.09 |
| 5 | 6.13E+04 | 27.71 |
| Std. 10^6 | 1.00E+06 | 19.67 |
| Std. 10^5 | 1.00E+05 | 21.95 |
| Std. 10^3 | 1.00E+03 | 27.57 |
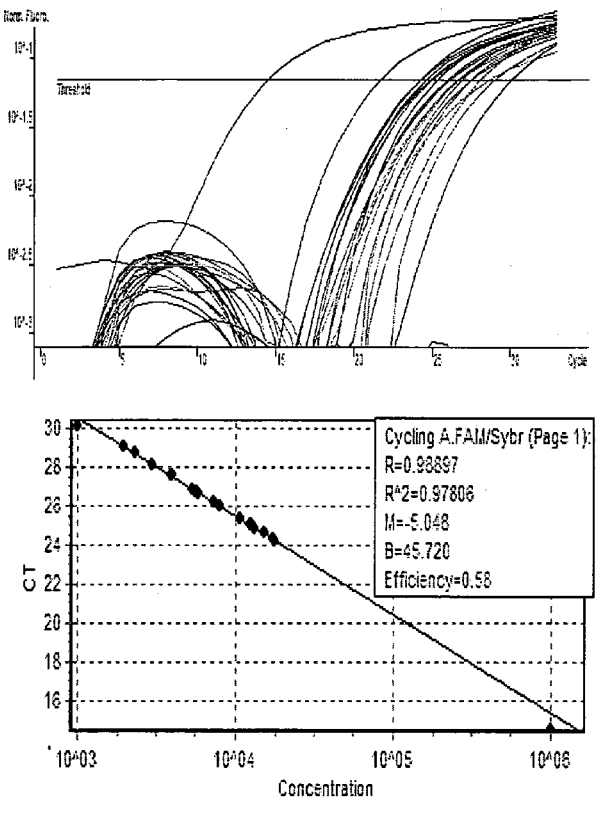
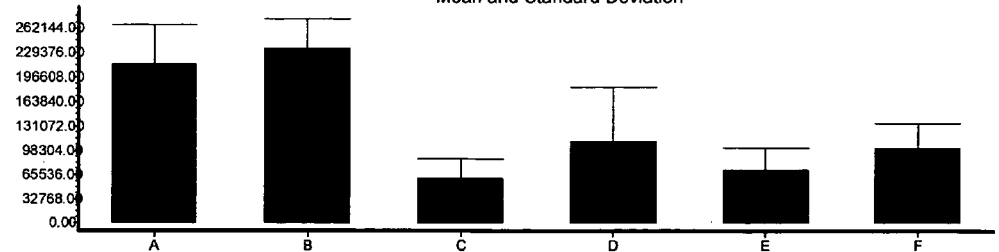
Ureaplasma urealyticum
Mean and Standard Deviation
ANOVA    p=0.0017

INTEGRATED METHOD FOR COLLECTION AND MAINTENANCE OF DETECTABILITY OF A PLURALITY OF MICROBIOLOGICAL AGENTS IN A SINGLE CLINICAL SAMPLE AND FOR HANDLING A PLURALITY OF SAMPLES FOR REPORTING A SUM OF DIAGNOSTIC RESULTS FOR EACH SAMPLE

CROSS REFERENCES TO RELATED APPLICATIONS

The present application claims benefit, under 35 U.S.C. 119(e), to U.S. Provisional Application No. 60/651,688, entitled "A Method and Kit for the Collection and Maintenance of the Detectability of a Plurality of Microbiological Species in a Single Gynecological Sample," filed on Feb. 10, 2005, the entire contents of which are hereby incorporated by reference. Additionally, the present application claims benefit, under 35 U.S.C. 119(e), to U.S. Provisional Application No. 60/654,485, entitled "Integrated Method for Collection and Maintenance of Detectability of a Plurality of Microbiological Agents in a Single Clinical Sample and for Handling a Plurality of Samples for Reporting a Sum of Diagnostic Results for Each Sample," filed on Feb. 18, 2005, the entire contents of which are hereby incorporated by reference. Also, the present application claims benefit, under 35 U.S.C. 119(e), to U.S. Provisional Application No. 60/654,729, entitled "A Method of Receiving and Handling a Plurality of Clinical Samples for Reporting a Sum of Diagnostic Results for Each Sample," filed on Feb. 18, 2005, the entire contents of which are hereby incorporated by reference.

BACKGROUND OF THE INVENTION

1. Field of the Invention

The present invention is in the field of clinical diagnostic services, i.e., in the industry of identification, characterization, quantification of biological agents associated with disease conditions. The present invention is particularly directed toward a method and materials for the collection and maintenance of detectability of a plurality of species of microbiological agents selected from the group consisting of bacteria, fungi, viruses, and protozoa in a single clinical sample and managing information associated with a plurality of samples for reporting a sum of diagnostic results for each sample.

2. Description of the Related Art

Clinical diagnostics provide an essential aid to the physician for the diagnosis and monitoring of numerous pathologies and infectious diseases. Rapid and accurate identification of causative agents of a myriad of different human pathophysiological conditions is a paramount requisite to effective treatment.

A biological sample generally is taken from the patient, most often at the request of a physician, and sent to a medical laboratory for analysis to establish or confirm a diagnosis of clinical symptoms. A physician may suspect a particular causative agent upon physical examination. However, certain symptoms may be characteristic of a plethora of different causative agents. Therefore, due to misdiagnoses of causative agents, patients may be treated non-efficaciously. Moreover, in other instances, a physician may request a certain diagnostic test to be performed on a clinical specimen wherein the test subsequently produces a negative result. Then, of course, further clinical samples and diagnostic testing are required. In many instances, due to the lack of timely and accurate diagnoses, patients' original conditions progress to the further detriment of treatability and to the well-being of the patient. Accurate clinical diagnosis is critical to specifically identify causative agents in a timely manner which mediates pathophysiological conditions. Accordingly, a need indeed exists for materials and a method, for example, to collect an accurate clinical sample, e.g. a "snapshot," representative of vaginal flora, i.e., a certain gynecological microbiological environment, and maintain the detectability of a plurality of species in a single gynecological sample.

Diagnostic kits are available, for example, capable of detecting several specific species. However, in many instances current diagnostic products and services are inadequate to identify the causative agent or are inoperable under clinical circumstances.

Advances in the detection of *C. trachomatis* and *N. gonorrhoeae*, for example, have included the development of nucleic acid amplification tests from cervical as well as urine samples. The Roche COBAS AMPLICOR™ CT/NG Test, for example, is an in vitro multiplex diagnostic test that can detect either or both *Chlamydia trachomatis* or *Neisseria gonorrhoeae* in endocervical or urethral swabs and/or urine samples. The COBAS AMPLICOR™ Analyzer is an instrument which automates amplification and detection of the PCR process. The test utilizes polymerase chain reaction (PCR) nucleic acid amplification and nucleic acid hybridization (Roche Diagnostic Systems, Branchburg, N.J.). APTIMA COMBO 2 Assay is a Gen-Probe nucleic acid amplification test that uses target capture for in vitro qualitative detection and differentiation of rRNA from *C. trachomatis* and *N. gonorrhoeae* in endocervical and male urethral swab specimens and in urine specimens. The assay uses target capture (TC), Transcription-Mediated Amplification (TMA) and Dual Kinetic Assay (DKA) (Gen-Probe, Inc., San Diego, Calif.).

However, in view of the myriad of different pathological agents that mediate disease conditions, a need indeed exists for materials and methods to collect an accurate clinical sample, e.g. a "snapshot," representative of a certain gynecological microbiological environment, for example, and maintain the detectability of the diversity of pathological agents in a single gynecological sample. Methods are particularly needed for receiving and handling a plurality of single gynecological swab clinical samples, each having identity and test requisition information associated therewith, wherein the test requisition information indicates a test for at least one causative agent from a plurality of listed agents, and managing information associated therewith for reporting a sum of diagnostic results for each sample.

BRIEF SUMMARY OF THE INVENTION

The present invention is directed to methods and materials for the collection and maintenance of detectability of a plurality of species of microbiological agents indicative of a gynecological disorder selected from the group consisting of bacteria, fungi, viruses and protozoa, in a single gynecological sample comprising providing transport media in a resealable container, a sterile swab, and instructions for preparation and handling of a gynecological sample, and an indication of the detectability of the plurality of species. The current invention is particularly directed to receiving a plurality of these gynecological swab samples and managing material and information associated with the samples for reporting a sum of diagnostic results for each sample.

Embodiments of the present invention are preferred wherein at least one species within the plurality of species is indicative of at least one gynecological disorder, e.g., wherein at least one species within the plurality of species is selected from the group consisting of *Bacteroides fragilis, Candida albicans, Candida glabrata, Candida parapsilosis, Candida tropicalis, Chlamydia trachomatis, Gardnerella vaginalis, Haemophilis ducreyi*, Herpes simplex virus subtype 1 (HSV-1), *Herpes simplex virus subtype 2* (HSV-2), Human papillomavirus (HPV), *Mobiluncus mulieris, Mobiluncus curtisii, Molluscum contagiosum* Virus, *Mycoplasma genitalium, Mycoplasma hominis, Neisseria gonorrhoeae, Treponema pallidum, Trichomonas vaginalis, Ureaplasma urealyticum*, and *Streptococcus agalactiae* (Group B Streptococcus). Methods are preferred wherein at least two (2), three (3), four (4), five (5), or six (6) species within the plurality of species are selected from the group.

The present invention is directed to a method of receiving and handling a plurality of clinical samples and managing information associated therewith for generating and reporting any of a plurality of different diagnostic results from each sample in a timely manner, particularly within about thirty (30) hours.

The present invention is directed to a method for the collection and maintenance of detectability of a plurality of species of microbiological agents selected from the group consisting of bacteria, fungi, and viruses, in a single clinical sample and for handling a plurality of samples and managing information associated therewith for reporting a sum of diagnostic results for each sample comprising the steps of:

(a) providing transport media in a resealable container with instructions for preparation and handling of a sample and an indication of the detectability of the plurality of species;

(b) receiving a plurality of samples, each having identity and test requisition information associated therewith wherein the test requisition information indicates a test for at least one species from a plurality of species;

(c) entering the information into a system to create a requisition file for each sample;

(d) processing the information to create a list of samples to be tested for each species;

(e) dispensing an aliquot corresponding to each sample into an individual vessel, to create a secondary sample, for each designated test for different species on each sample;

(f) assembling a general supply of master reagent mix for each different test;

(g) combining an aliquot of master reagent mix for each test with each corresponding secondary sample to produce a diagnostic test reaction for each secondary sample;

(h) determining the presence or absence of a certain product of each reaction to produce a result, recording the result of each reaction;

(i) combining the result of each reaction derived from each primary sample into the requisition file for each sample on the system, thereby producing a sum of results for each sample; and (j) reporting the results;
wherein the plurality of species comprises at least one species selected from the group consisting of Molluscum contagiosum virus, *Mycoplasma genitalium, Mycoplasma hominis, Candida dubliniensis, Candida krusei, Candida lusitaneae, Atopobium vaginae*, erythromycin-resistant *Streptococcus agalactiae*, clindamycin-resistant *Streptococcus agalactiae, Lymphogranuloma venereum*, HPV-16, HPV-18, HPV-31, HPV-33, HPV-35, HPV-39, HPV-45, HPV-51, HPV-52, HPV-56, HPV-58, HPV-59, HPV-66, HPV-68, HPV-6/11, HPV-42, HPV-43, and HPV-44.

The present invention is directed to a method for the collection and maintenance of detectability of a plurality of species of microbiological agents selected from the group consisting of bacteria, fungi, and viruses, in a single gynecological sample and for handling a plurality of samples and managing information associated therewith for reporting a sum of diagnostic results for each sample comprising the steps of:

(a) providing a kit comprised of transport media in a resealable container, a sterile swab, and instructions for preparation and handling of a gynecological sample and a writing which indicates the detectability of the plurality of species;

(b) receiving a plurality of samples, each derived from the kit, having identity and test requisition information associated therewith wherein the test requisition information indicates a test for at least one species from the plurality of species;

(c) entering the information into a system to create a requisition file for each sample;

(d) processing the information to create a list of samples to be tested for each species;

(e) dispensing an aliquot corresponding to each sample into an individual vessel, to create a secondary sample, for each designated test for different species on each sample;

(f) assembling a general supply of master reagent mix for each different test;

(g) combining an aliquot of master reagent mix for each test with each corresponding secondary sample to produce a diagnostic test reaction for each secondary sample;

(h) determining the presence or absence of a certain product of each reaction to produce a result, recording the result of each reaction;

(i) combining the result of each reaction derived from each primary sample into the requisition file for each sample on the system, thereby producing a sum of results for each sample; and (j) reporting the results,
wherein the plurality of species comprises at least one species selected from the group consisting of Molluscum contagiosum virus, *Mycoplasma genitalium, Mycoplasma hominis, Candida dubliniensis, Candida krusei, Candida lusitaneae, Atopobium vaginae*, erythromycin-resistant *Streptococcus agalactiae*, clindamycin-resistant *Streptococcus agalactiae, Lymphogranuloma venereum*, HPV-16, HPV-18, HPV-31, HPV-33, HPV-35, HPV-39, HPV-45, HPV-51, HPV-52, HPV-56, HPV-58, HPV-59, HPV-66, HPV-6/11, HPV-42, HPV-43, and HPV-44.

BRIEF DESCRIPTION OF THE DRAWINGS

FIG. 1 is an example of a Test Requisition Form.

Lanes 17-19 represent detectability after storage at room temperature for five days. Lanes 20 and 21 are the positive and negative controls, respectively.

Figure 3:
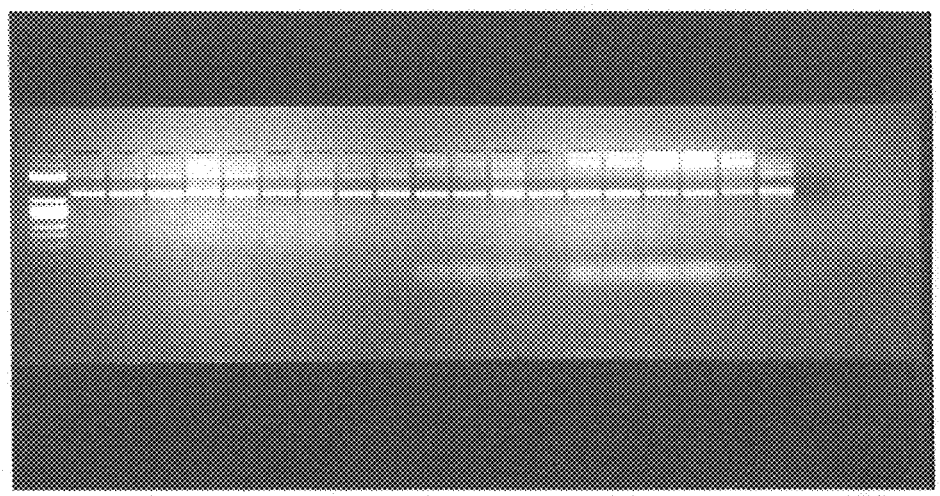

FIG. 3 displays validation data for *Mobiluncus mulieris* wherein the PCR amplicon is 1015 bp in which each sample was independently inoculated and extracted in triplicate. Lanes 2-4 represent detectability after storage at room temperature for zero days. Lanes 5-7 represent detectability after storage at room temperature for one day. Lanes 8-10 represent detectability after storage at room temperature for two days. Lanes 11-13 represent detectability after storage at room temperature for three days. Lanes 14-16 represent detectability after storage at room temperature for four days. Lanes 17-19 represent detectability after storage at room temperature for five days. Lanes 20 and 21 are the positive and negative controls, respectively.

FIG. 4 displays validation data for *Candida albicans*.
FIG. 5 displays validation data for *Candida glabrata*.
FIG. 6 displays validation data for *Candida parapsilosis*.
FIG. 7 displays validation data for *Candida tropicalis*.
FIG. 8 displays validation data for *Chlamydia trachomatis*.
FIG. 9 displays validation data for *Gardnerella vaginalis*.
FIG. 10 displays validation data for *Haemophilis ducreyi*.
FIG. 11 displays validation data for HSV-1.
FIG. 12 displays validation data for HSV-2.
FIG. 13 displays validation data for *Trichomonas vaginalis*.
FIG. 14 displays validation data for *Ureaplasma urealyticum*.

DETAILED DESCRIPTION

Unless defined otherwise, all technical and scientific terms used herein have the same meaning as is commonly understood by one of skill in the art to which this invention belongs. All publications and patents referred to herein are incorporated by reference.

Physicians are generally faced with observing patients' symptoms, obtaining biological samples, and ordering clinical diagnostic tests to determine the identity of causative agents which mediate pathological conditions. Since methods of treatment of pathophysiological conditions are intimately related to the identity of the causative agent(s) of the condition, rapid and accurate identification and reporting of the causative agent(s) is of paramount importance to the practice of medicine today. The present invention enables the accurate and rapid reporting of the detection of any of a plurality of biological agents from each clinical sample.

It is an object of the present invention to provide methods and materials for the collection and maintenance of detectability of a plurality of species of microbiological agents indicative of a gynecological disorder in a single gynecological sample comprising providing transport media in a resealable container, a sterile swab, instructions for preparation and handling of a gynecological sample, and an indication of the detectability of a plurality of species. It is also an object of the present invention to integrate a method of handling a plurality of these samples and managing information associated therewith for reporting a sum of diagnostic results for each sample.

The present invention is fundamentally a method for providing certain materials for the collection and maintenance of detectability of a plurality of species of microbiological agents indicative of a gynecological disorder in a single gynecological sample and receiving and handling a plurality of the clinical samples resulting therefrom and managing material and information associated therewith for generating and reporting a sum of diagnostic results for each sample.

The flow of information and reporting of results from a clinical laboratory is a fundamental aspect of the present invention. The present invention enables the accurate and rapid reporting of the detection of any of a plurality of biological agents from each clinical sample. The present invention is also a method for receiving and handling a plurality of clinical samples and managing information associated therewith to effect rapid diagnostic testing for any of a plurality of agents in each sample. Although the invention defined by the claims appended hereto are not necessarily so limited, preferred methods of the invention are for handling a plurality of single gynecological swabs (e.g., each from a different patient) and managing information associated therewith.

A basic embodiment of the method of the present invention involves a rapid method of handling a plurality of single gynecological swab samples and managing information associated therewith for reporting any of a plurality of different diagnostic results for each sample within about fifty (50) hours of receiving the sample (preferably within forty eight (48) hours, more preferably within about thirty (30) hours, most preferably within about twenty four (24) hours). Single gynecological swab samples each have identity and test requisition information associated therewith, wherein the test requisition information indicates a test for at least one causative agent, from a choice of a plurality of agents (for example, between about 5 and about 25 different microbiological agents). The term "causative agent" as used herein refers to biological entities that mediate disease conditions, including, but not limited to, microorganisms, e.g., bacteria, fungi, and viruses. Preferred agents, referred to herein as causative agents, include but are not limited to microbiological species associated with pathological gynecological conditions, for example, collected in a single swab specimen (clinical sample). Causative agents referred to herein include, but are not limited to *Bacteroides fragilis, Candida albicans, Candida glabrata, Candida parapsilosis, Candida tropicalis, Chlamydia trachomatis, Gardnerella vaginalis, Haemophilis ducreyi*, Herpes simplex virus subtype 1 (HSV-1), Herpes simplex virus subtype 2 (HSV-2), Human papillomavirus (HPV), *Mobiluncus mulieris, Mobiluncus curtisii, Molluscum contagiosum* Virus, *Mycoplasma genitalium, Mycoplasma hominis, Neisseria gonorrhoeae, Treponema pallidum, Trichomonas vaginalis, Ureaplasma urealyticum*, and *Streptococcus agalactiae* (Group B Streptococcus), for example.

Proper and timely identification of causative agent(s) of vaginosis, a massive microecologic alteration of the vaginal flora, is a continuous problem for obstetrician-gynecologists. Bacterial vaginosis (BV), for example, is related to considerable and preventable infectious morbidity in non-pregnant women. Bacterial vaginosis mediates endometritis, pelvic inflammatory disease, post-surgical abortion infections, post-hysterectomy infections, an increased risk of HIV acquisition and cervical intraepithelial neoplasia. The diagnosis of BV is complicated by the polymicrobial nature of the condition. Bacterial Vaginosis (BV), for example, is characterized by a logarithmically increased concentration of *Gardnerella vaginalis* and logarithmically increased concentrations of pathogenic bacteria, including *Bacteroides* spp., *Mobiluncus* spp., along with *Ureaplasma urealyticum* and *Mycoplasma* spp. *Bacteroides fragilis* is an anaerobic bacterium that is commonly associated with BV. *Mobiluncus* species, e.g., *Mobiluncus mulieris* and *Mobiluncus curtisii*, are anaerobic bacteria that are commonly associated with BV. Fifty percent of patients diagnosed with BV, however, display no symptoms.

Mycoplasmas are small (0.2-0.3 nm) membrane bound organisms capable of independent self-replication. The most prevalent strains recoverable from the genital tract are *Ureaplasma urealyticum, Mycoplasma hominis* and *Mycoplasma genitalium*. In some pregnant women, *Ureaplasma* infections are considered to be the cause of chorioamnionitis and premature delivery. They are frequently transmitted from mothers to their infants, which may cause a variety of disorders including pneumonia, persistent pulmonary hypertension, and chronic infection of the central nervous system. *M. hominis* is associated with pyelonephritis, pelvic inflammatory disease (PID), spontaneous abortion, and postpartum septicemia and fever. *M. genitalium* has been associated with non-gonoccocal urethritis, acute endometritis, cervicitis, and pelvic inflammatory disease (PID). Infants become colonized with genital mycoplasmas during birth. Genital mycoplasma infections are usually diagnosed by culture. However, due to its fastidious slow-growing nature, *M. genitalium*, for example, may take up to eight (8) weeks to culture.

*Candida* Vaginitis (CV) is currently the second most common cause of vaginal infections, with bacterial vaginosis the most common diagnostic entity. However, CV is misdiagnosed in as much as 50% of all cases. Most studies indicate that CV is a frequent diagnosis among young women, affecting as many as 15% to 30% of symptomatic women visiting a clinician. *Candida albicans* is one of the major causes of *Candida* Vaginitis (CV). The widespread use of topical antifungals appears to contribute to selection for non-albicans yeasts, e.g., *C. glabrata* accounts for 7% of all vaginal fungal infections and about 10% of vaginal yeast isolates. *Candida tropicalis* is isolated from 1% to 5% of vaginal yeast isolates and may be associated with a higher rate of recurrence after standard treatment. *C. parapsilosis* accounts for 1% of vaginal yeast isolates.

*Chlamydia trachomatis* is the causative agent of a variety of diseases including trachoma and urogenital infections. It is the most common sexually transmitted bacterial agent and in women it causes cervicitis, urethritis, endometritis and salpingitis. In more complicated cases it may result in tubal scarring, infertility, and ectopic pregnancy. In men it causes urethritis and proctatitis. Other forms of infection also seen are trachoma, the most preventable form of blindness, and conjunctivitis in neonates.

*Neisseria gonorrhoeae* is the causative agent of the sexually transmitted disease gonorrhea. It is the most frequently reported communicable disease in the United States. In women, the most common presentation is endocervical infection. If left untreated it may develop into vulvovaginitis, salpingitis, and pelvic inflammatory disease (PID). Infections in men range from uncomplicated lower genital tract involvement such as urethritis, to the more serious epididymitis, prostatitis, and urethral stricture. Untreated asymptomatic infections may, in certain instances, develop into disseminated gonococcal infection (DGI).

Genitourinary tract infections due to *C. trachomatis* and *N. gonorrhoeae* are a major cause of morbidity in sexually active individuals. In males they may cause epididymitis and urethritis. In females, they can cause pelvic inflammatory disease (PID), ectopic pregnancy, and infertility. If left untreated, *N. gonorrhoeae* may develop into a disseminated gonococcal infection (DGI). Coinfection with *C. trachomatis* and *N. gonorrhoeae* is not uncommon. In fact, up to half of patients diagnosed with infection of one of these pathogens may be infected with the other and, therefore, it is important to test all sexually active individuals for both. Both sexually transmissible pathogens are detectable by swabbing the urethra and/or the cervix (for women) and performing either a culture and/or a nucleic acid amplification assay (see Van Doornum et al., 2001, Journal of Clinical Microbiology 39(3):829-835).

*Chlamydia trachomatis, Neisseria gonorrhoeae*, and *Trichomonas vaginalis* are the major causes of leukorrhea. *Neisseria gonorrhoeae* is the causative agent of the sexually transmitted disease gonorrhea. In women, the most common symptom of *N. gonorrhoeae* infection is endocervical infection, and if left untreated, may develop into vulvovaginitis and pelvic inflammatory disease. As a protozoan parasite, *Trichomonas vaginalis* is the causative agent of the sexually transmitted disease trichomoniasis. *T. vaginalis* infection is the primary cause of vaginitis, cervicitis and urethritis in women. Routine clinical diagnosis usually depends on microscopic identification of the parasite in wet mount preparations, which are only 60% sensitive as compared to culture-positive women.

The three major causes of Genital Ulcer Disease (GUD) are Herpes simplex virus, *Treponema pallidum* (syphilis), and *Haemophilis ducreyi* (chancroid). As treatment options vary, it is medically necessary to identify the causative agent of GUD. Currently, the diagnosis of GUD is based primarily on the clinical presentation of the ulcer itself. However, agent-specific diagnosis based solely on the clinical evaluations are often obscured by multiple and mixed infections. *T. pallidum* is the causative agent of the sexually transmitted disease syphilis. *T. pallidum* is one of the few major bacterial pathogens of humans that cannot be cultivated on artificial medium.

Human Papillomavirus (HPV) subtyping is of clinical significance in view of the growing evidence for the association of Human Papillomavirus (HPV) subtypes (i.e., HPV-16 and HPV-18) with cervical and ovarian cancer. Particularly, 90% of individuals with major grade cervical intraepithelial neoplasia (CIN 2 and CIN 3) and invasive carcinoma of the cervix are also infected with HPV-16 or HPV-18. Moreover, as much as 10% to 20% of women in the United States have tested positive to HPV by Papanicolaou (Pap) smear. Since Pap smears cannot differentiate among HPV subtypes, asymptomatic individuals that are HPV positive are being disregarded by the clinicians.

Molluscum contagiosum virus (MCV) is a member of the human pox viruses which produces small raised papules or lesions with central umbilications and a white, firm, curd-like core. Infection occurs during sexual intercourse. MCV is a common infection in the United States and accounts for approximately 1% of all undiagnosed skin disorders. Many physicians find it necessary to differentiate MCV from Human papillomavirus (HPV) or Herpes simplex virus (HSV) infections which have greater mortality and morbidity.

Vaginal Group B *Streptococcus* (*Streptococcus agalactiae*) (GBS), the most common cause of life-threatening infection in newborns, is a common cause of neonatal septicemia, pneumonia and meningitis. One out of every twenty babies with GBS dies from the infection. In pregnant women, GBS can cause bladder infections, womb infections, and stillbirth. Many adults are asymptomatic carriers of GBS in the bowel, vagina, bladder or throat. Diagnosis by traditional cultures may take several days to complete. However, once properly diagnosed, GBS can be treated with antibiotics to prevent the spread from mother to baby.

The term "clinical sample," as used herein, refers to biological samples known in the art. "Clinical sample" includes, for example, but is not limited to a gynecological swab sample. Particularly, the method of the present invention provides materials for the collection and maintenance of a "snapshot" of a gynecological environment for the detectability of a plurality of species of microbiological agents in a single gynecological sample. Clinical samples are generally labeled or otherwise clearly associated, e.g., packaged, with information that distinctly identifies the origin, source and/or destination for the results for each sample. Each sample is associated with an identifier, e.g., a patient's name, date of birth, and/or social security number, for example, or information otherwise provided by the source to indicate the distinct origin of each sample.

Methods described herein also comprise (1) providing a transport media in a resealable container, a sterile swab, and instructions for preparation and handling of a gynecological sample and a written indication of the detectability of the plurality of species, e.g., a test requisition form (see FIG. 1), (2) receiving the completed gynecological sample in a package with a completed test requisition form, and (3) handling a plurality of these clinical samples and managing information associated therewith for reporting any of a plurality of different diagnostic results for each sample in a timely manner. Reporting may be accomplished by means of facsimile to an attending physician who ordered the test(s), for example, or other means, electronic or otherwise, e.g., posting on a private-access internet web site, including all means that are usual and customary in the health-care industry.

The present invention is not drawn to methods for the detection, identification or diagnosis, per se, of any particular microbiological species, or series of species, or disease condition. The tests, per se, however, whatever tests are used, are not relevant to the subject matter of the present invention. In contrast, methods described herein are specifically directed toward collection and maintenance of detectability of a plurality of species of microbiological agents and handling a plurality of clinical samples and managing material and information associated therewith. Particularly, methods of the present invention are for providing a compilation of certain materials, managing samples and information related to the samples proximal in time, i.e., before, during, and after, a determination of any of a plurality of different possible diagnostic results for each sample and reporting the results.

EXEMPLARY EMBODIMENT

The Applicants describe herein methods and materials to collect and maintain the detectability of multiple pathogens from a single gynecological swab. Specimen viability has been validated for up to five days, for example, as illustrated herewith. Longer viability, however, e.g., about 5-10 days, is reasonably expected in view of the data presented herein. No refrigeration is required. The present invention is not drawn to methods for the detection, identification or diagnosis, per se, of any particular microbiological species, or series of species, or disease condition. In contrast, methods and articles of manufacture, i.e., kits, of the present invention are particularly provided for the collection and maintenance of detectability of a plurality of different microbiological species associated with pathological gynecological conditions so that a clinical diagnostic service provider, for example, may enable a physician to collect a single swab specimen (clinical sample) and order any of a plurality of tests on that sample from the clinical diagnostic service provider, for example. The tests, per se, however, whatever-tests are used, are not relevant to the subject matter of the present invention. The Applicants indeed present validation data herewith merely to demonstrate the viability of the species exemplified herein using the materials and methods of the present invention. Since the species exemplified herein are well characterized in the art and are, as discovered and illustrated by the Applicants, viable under the conditions described herein, they are indeed detectable by an array of different methods, e.g., nucleic acid amplification, known to those of skill in the art.

A method is particularly preferred for the collection and maintenance of detectability of a plurality of species of microbiological agents selected from the group consisting of bacteria, fungi, and viruses, in a single gynecological sample comprising providing transport media in a resealable container, a sterile swab, and instructions for preparation and handling of a gynecological sample and an indication of the detectability of the plurality of species.

Microbiological agents that are causative or are otherwise associated with gynecological disorders are preferred. Since many different species of microbiological agents mediate, or are associated with, or are indicative of gynecological disorders, the present invention provides a means for handling a plurality of clinical gynecological swab samples and managing information associated therewith in the process leading up to the identification of at least one causative agent in each sample and reporting the results representative of the ambient population of microbiological agents in each sample at the time each sample was taken. Particularly, the method of the present invention enables a "snapshot" of details corresponding to each a single gynecological sample, within a plurality of samples, to be provided in a valuable period of time by means of information management. A single gynecological swab sample is generally received in transport media, between about 1 ml and about 5 ml, for example, in a resealable container along with a test requisition form.

Transport media for use in methods of the present invention is a universal transport media in which viability of a plurality of organisms, e.g., bacteria, fungi, and viruses, can be sustained under normal conditions without refrigeration for at least 48 hours. Transport media for use in methods of the present invention is preferred wherein the detectability of species selected from the group consisting of *Bacteroides fragilis, Candida albicans, Candida glabrata, Candida parapsilosis, Candida tropicalis, Chlamydia trachomatis, Gardnerella vaginalis, Haemophilus ducreyi,* Herpes simplex virus subtype 1 (HSV-1), Herpes simplex virus subtype 2 (HSV-2), Human papillomavirus (HPV), *Mobiluncus mulieris, Mobiluncus curtisii,* Molluscum contagiosum Virus, *Mycoplasma genitalium, Mycoplasma hominis, Neisseria gonorrhoeae, Treponema pallidum, Trichomonas vaginalis, Ureaplasma urealyticum,* and *Streptococcus agalactiae* (Group B *Streptococcus*) is maintained at room temperature for five (5) days.

An example of a general support media for a variety of organisms in a clinical sample is Stuart's medium (see, e.g., Stuart et al., 1954, The problem of transport of specimens for culture of Gonococci. Canadian Journal of Public Health. 45(2):73-83). Stuart's medium is a well-known buffered transport medium which includes the component sodium glycerophosphate to permit minimal multiplication and sodium thioglycollate as a reducing agent to prevent oxidation within the sample. Stuart's medium, however, contains no nutrients. The absence of nutrients retards the growth of commensal organisms within the sample which can multiply and overgrow the less hardy pathogens. However, the absence of nutrients in Stuart's media can be detrimental to the viability of less hardy pathogens. Preferred transport medium comprises an aqueous balanced salt solution buffered at approximately physiological pH, at least one protein stabilizer, and combinations of carbohydrate and amino acid nutrient sources. The medium is buffered to maintain physiological pH and may include a pH indicator in order to indicate variation of pH outside the physiological pH range. The medium further comprises antimicrobial and antifungal agents and can include gelatin. Transport media, for example, is liquid media wherein detectability of a plurality of species of microbiological agents including bacteria, fungi, and viruses is maintainable under normal conditions, without refrigeration, for at least 72 hours. Example transport media herein is demonstrated to be suitable for maintaining the detectability, for example, of a plurality of species of microbiological agents including bacteria, fungi, and viruses under normal conditions, without refrigeration, for about five (5) days (e.g., UTM-RT Transport Medium, Copan Diagnostics Inc., Corona, Calif.).

Transport medium, for example, consists of modified Hank's balanced salt solution supplemented with bovine serum albumin, cysteine, gelatin, sucrose, and glutamic acid. The pH is buffered with HEPES buffer, for example. Phenol red is used to indicate pH. Vancomycin, amphotericin B, and colistin are incorporated in the medium to inhibit growth of competing bacteria and yeast. The medium is isotonic and non-toxic to human cells. Example components comprise, for example, Hank's Balanced Salts, Bovine Serum Albumin, L-Cysteine, Gelatin, Sucrose, L-Glutamic Acid, HEPES Buffer, Vancomycin, Amphotericin B, Colistin, and Phenol Red; pH 7.3±0.2@25° C. Antimicrobial compositions can include vancomycin, gentamicin, colistin, or amphotericin B.

A general transport medium of about 1.0 liter (total volume) may be prepared in the following aqueous composition: gelatin, 0-20.0 g; sugar, 65-75 g; HEPES, 5-7 g; KCl, 0.3-0.6 g; L-glutamic acid, 0.5-1.0 g; phenol red, 5-15 mg; $CaCl_2$, 0.1-0.5 g; $MgSO_4$-7$H_2O$, 0.1-0.3 g; bovine serum albumin V, 1.0-20.0 g; vancomycin, 0.01-0.05 g; colistin, 100,000-250,000 units; and amphotericin B, 0.5-3.0 mg.

An example may include the following ingredients in about 995 ml of water q.s. 1 liter: sucrose, 68.46 g; HEPES, 5.96 g; KCl, 0.4 g; L-glutamic acid, 0.72 g; phenol red, 11.0 mg; $CaCl_2$, 0.27 g; $MgSO_4$-7$H_2O$, 0.20 g; BSA, 5.0 g; gelatin, 5.0 g; vancomycin, 0.025 g; colistin, 200,000 units; and amphotericin B, 1.0 mg. The pH of the medium can be adjusted with acidic or basic solutions to arrive at a final pH within physiological limits (see, e.g., U.S. Pat. No. 5,702,944, entitled Microbial Transport Media, which is herein incorporated by reference in its entirety).

Preferred commercially available and validated examples of transport medium for use in methods and articles of the present invention include, for example, the following: UTM-RT Transport Medium, BD Cellmatics Viral Transport Medium® (Becton, Dickinson & Company, Sparks, Md.), Multitrans Culture Collection and Transport System (Starplex Scientific, Etobicoke, Ontario, Canada), The ThinPrep® Pap Test Preservcyt® Solution (CYTYC Corporation, Boxborough, Mass.), SurePath® (Tripath Imaging Inc., Burlington, N.C.).

Preferred methods of the present invention provide a transport media in a resealable container, a sterile swab, instructions for preparation and handling of a gynecological sample and a written indication of the detectability of the plurality of species.

A labeled screw-cap tube is preferred, for example, as a resealable container, which contains a volume of transport medium, between about 1 ml and about 5 ml, for example, suitable for accurate collection and maintenance of a population of microbiological agents representative of a gynecological environment. A resealable container optionally contains glass beads (three 3 mm beads, for example). Although not required to be provided, per se, in methods and the specified compilation of materials described herein, at least one sterile swab, well-known in the art of gynecology, is preferred in the materials of a packaged kit described herein for obtaining the gynecological sample. At least one sterile swab for obtaining the gynecological sample, for example, is preferably supplied with the transport media in a package along with written instructions for preparation and handling of a gynecological sample in the media, and a written indication of the detectability of a plurality of species, e.g., a test requisition form. The transport medium may be supplied, however, alone in a package which comprises a writing, i.e., a written indication of the detectability of a plurality of species, for example, a test requisition form which lists a plurality of species of microbiological agents described herein for selection, for example, by the attending physician. The compilation of materials described herein is preferably provided in methods described herein in a container, i.e., a package. The package preferably contains the materials in a kit-format. Written instructions for preparation and handling of a gynecological sample in the media are preferred to be included in the compilation of materials otherwise described herein as a packaged kit intended, designated, and prepared for the specific purpose of collection and maintenance of detectability of a plurality of species of microbiological agents described herein. Once a swab sample is collected, it should be placed immediately into the transport tube where it comes into contact with transport medium.

A first set of example instructions are as follows:
1. Collect the single specimen with a swab (Polyester (Dacron) tipped swabs are suitable).
2. Aseptically remove the cap from the transport media.
3. Insert swab into the tube with the transport medium.
4. Break swab shaft by bending it against the tube wall.
5. Replace cap to tube and close tightly.
6. Label the tube with appropriate patient information.
7. Complete the test requisition form included herewith.
8. Send these items in the pre-addressed postage materials included herewith to the laboratory for immediate analysis.

A second set of example instructions are as follows:
1. Visualize cervix with speculum without lubricant.
2. Remove mucus and/or secretions from the cervix with a swab, discard swab.
3. Firmly, yet gently, sample the endocervical canal with sterile swab for 10 seconds.
4. Place the swab into the transport vial.
5. Be sure the cap is sealed tightly.

Specimen collection swab options include, for example: one regular size plastic shaft swab with polyester fiber tip; two regular size plastic shaft swabs with polyester fiber tips; one regular size plastic shaft swab and one Minitip plastic shaft swab pre-scored for easy breakage, both with polyester fiber tips; one Minitip plastic shaft swab with polyester fiber tip pre-scored for easy breakage; one Combo stainless steel wire-plastic shaft Minitip swab with polyester fiber tip: one regular size plastic shaft swab and one Combo stainless steel wire-plastic shaft Minitip swab, both with polyester fiber tips. These different swab applicator shafts facilitate the collection of specimens from various sites on a patient.

Receiving a Plurality of Single Gynecological Swab Samples

A "plurality of samples" is an inclusive term which refers to a plurality of single samples from different patients. A "plurality" of samples generally refers to a substantial number of biological samples received by a clinical lab within a twenty four (24) hour period, for example. A plurality of samples, however, as used herein may refer to as few as several samples, e.g., about ten (10), or about five thousand (5,000) samples, for example, to be processed. Each sample has identity and test requisition information associated therewith, wherein the test requisition information indicates a test for at least one causative agent, from a choice of a plurality of agents, from a list of between about 5 and about 25 different microbiological agents, for example. For the purpose of illustration of the complexity of information associated with a plurality of single gynecological swabs and test requisition information associated therewith, each sample with a test requisition form which indicates the detectability of twenty (20) different agents, for example, has the possibility of about 400 different diagnostic results, for that single sample. This, combined with the fact that a plurality of samples (e.g., 500) are received to be processed together, that day, illustrates the complexity of information associated therewith to be managed in order to handle the plurality of clinical samples for reporting any of a plurality of different diagnostic results for each sample in a timely manner. The current invention is particularly directed to methods wherein the test requisition information indicates a test for at least one (1), preferably at least two or three (2 or 3), e.g., between 4 and about 6, causative agents from a choice (list) of a plurality of agents. Embodiments of the present invention include, for example, wherein the plurality of species comprise at least one species selected from the group consisting of Molluscum contagiosum Virus, *Mycoplasma genitalium*, and *Mycoplasma hominis*.

The information in the system, i.e., the identity of the sample (e.g., sample identifier or identification tag) and test requisition information, i.e., tests specifically requested to be performed on that sample, is processed to designate a test on each sample for at least one causative agent. Accordingly, methods described herein comprise entering identity and test requisition information associated with each sample into a system to create a requisition file for each sample. The term "system" as used herein refers generally to a system of recording and managing information, a computer implemented information management system to manage the flow of information and, in certain embodiments, to control instrumentation, throughout the process of the present invention. This system is preferred, but, however, is not required. A computer is generally employed to receive the identity and test requisition information associated with each sample. The information may be entered manually into a server, for example, to create a test requisition file for each sample which comprises the sample information and the test requisition information. A listing, file for example, of the identity of all samples for each test is created. If twenty different tests are to be performed (for twenty different pathological agents), for example, twenty different lists of sample identifiers are created. If a certain sample will be subject to three different tests, for example, that sample identifier will be on at least three separate lists corresponding to those three different tests. In some embodiments of the present invention a computer implemented system performs calculations and/or controls instrumentation.

A method for the collection and maintenance of detectability of a plurality of species of microbiological agents selected from the group consisting of bacteria, fungi, and viruses, in a single clinical sample and for handling a plurality of samples and managing information associated therewith for reporting a sum of diagnostic results for each sample is preferred which comprises providing transport media in a resealable container with instructions for preparation and handling of a sample and an indication of the detectability of the plurality of species, receiving a plurality of samples, each having identity and test requisition information associated therewith wherein the test requisition information indicates a test for at least one species from a plurality of species, entering the information into a system to create a requisition file for each sample, processing the information to create a list of samples to be tested for each species, dispensing an aliquot corresponding to each sample into an individual vessel, to create a secondary sample, for each designated test for different species on each sample, assembling a general supply of master reagent mix for each different test, combining an aliquot of master reagent mix for each test with each corresponding secondary sample to produce a diagnostic test reaction for each secondary sample, determining the presence or absence of a certain product of each reaction to produce a result, recording the result of each reaction, combining the result of each reaction derived from each primary sample into the requisition file for each sample on the system, thereby producing a sum of results for each sample, and reporting the results. Methods are particularly preferred wherein at least one species within the plurality of species is indicative of at least one gynecological disorder. Methods of the present invention are preferred wherein the plurality of species comprises *Chlamydia trachomatis* and *Neisseria gonorrhoeae*. Methods of the present invention are preferred wherein the plurality of species comprises *Gardnerella vaginalis, Mobiluncus mulieris, Mobiluncus curtisii*, and *Bacteroides fragilis*. Methods of the present invention are preferred wherein the plurality of species comprises *Candida albicans, Candida glabrata, Candida parapsilosis*, and *Candida tropicalis*. Methods of the present invention are preferred wherein the plurality of species comprises *Mycoplasma genitalium, Mycoplasma hominis*, and *Ureaplasma urealyticum*. Methods of the present invention are preferred wherein the plurality of species comprises Herpes simplex virus, *Treponema pallidum*, and *Haemophilis ducreyi*. Methods of the present invention are preferred wherein at least one (1) species of the plurality of species is selected from the group consisting of Molluscum contagiosum Virus, *Mycoplasma genitalium*, and *Mycoplasma hominis*.

Nucleic Acid is Extracted from Each Sample

Established procedures for DNA extraction are used (see Example II). In brief, swabs are thoroughly mixed in the transport media contained within the transport vials. 470 μl of transport media is mixed with 25 μl of 10% sodium dodecyl sulfate, and 12 μl of freshly prepared DNase-free proteinase-K (10 mg/ml), then incubated for 2 hours at 55° C. DNA is phenol:chloroform:isoamyl alcohol extracted and recovered by ethanol precipitation. DNA is pelleted, dried in a speed vacuum, and resuspended in 20 μl TE buffer. DNA concentration is calculated by absorbance 260/280 readings and was adjusted to 0.2 μg/μl prior to PCR analysis. Quantitation, however, is preferred using a fluorometer. Quantitation, however, is preferred using a fluorometer such as one available from Turner BioSystems, Inc., Sunnyvale, Calif.

The nucleic acid from each sample is diluted to about 200 ng/µl, for example, with water, for example, to provide a standardized primary nucleic acid solution corresponding to each sample. An aliquot of nucleic acid from each sample is dispensed into a separate individual vessel to create a secondary sample corresponding to each designated test on each sample. A general supply of master reagent mix, e.g., real-time PCR mix, for each test for each different causative agent is prepared. An aliquot of each master reagent mix is combined with each corresponding secondary nucleic acid sample for each test to produce a diagnostic test reaction for each secondary sample. Each reaction is incubated and preferably monitored in real-time. The presence or absence of a certain product of each reaction to produce a result is determined. The result of each reaction is recorded in the system. The result of each reaction derived from each primary solution is combined into the requisition file for each sample on the system, thereby identifying at least one causative agent in each sample, and the results of the identification are reported.

A rapid method of handling a plurality of clinical samples and managing information associated therewith for identifying at least one causative agent in each sample and reporting results comprises receiving a plurality of samples, each having identity and test requisition information associated therewith wherein the test requisition information indicates a test for at least one causative agent, entering the information into a system to create a requisition file for each sample, processing the information to designate a test on each sample for at least one causative agent, dispensing an aliquot corresponding to each sample into an individual vessel to create a secondary sample for each designated test, assembling a general supply of master reagent mix for each test for a different causative agent, combining an aliquot of each master reagent mix with each corresponding secondary sample for each test to produce a diagnostic test reaction for each secondary sample, incubating each reaction, determining the presence or absence of a certain product of each reaction to produce a result, recording the result of each reaction, combining the result of each reaction derived from each primary sample into the requisition file for each sample on the system, thereby identifying at least one causative agent in each sample, and reporting the results of the identification.

A preferred method of handling a plurality of clinical samples and managing information associated therewith for identifying at least one causative agent in each sample and reporting results comprises receiving a plurality of samples, each having identity and test requisition information associated therewith wherein the test requisition information indicates a test for at least one causative agent, entering the information into a system to create a requisition file for each sample, extracting nucleic acid from each sample, quantitating the nucleic acid, diluting the nucleic acid from each sample to provide a standardized primary nucleic acid solution corresponding to each sample, processing the information in the system to designate a real-time PCR test on each nucleic acid for at least one causative agent, dispensing an aliquot of the primary solution from each sample into a separate individual vessel to create a standardized secondary nucleic acid sample for each designated test on each sample, assembling a general supply of master reagent mix for each test for a different causative agent, combining an aliquot of each master reagent mix with each corresponding secondary nucleic acid sample for each test to produce a diagnostic test reaction for each secondary sample, incubating each reaction, determining the presence or absence of a certain product of each reaction to produce a result, electronically recording the result of each reaction, in the system, combining the result of each reaction derived from each primary solution into the requisition file for each sample on the system, thereby identifying at least one causative agent in each sample, and reporting the results of the identification. Preferred methods of the invention described herein employ quantitating nucleic acid from each sample by means of a fluorometer. Methods of the present invention preferably comprise generation of diagnostic results by means of real-time PCR.

To Maximize the Success of Clinical Diagnostic Methods Described Herein

A clinical diagnostic laboratory should be physically set up so that specimen separation and extractions occur in a separate room, using a "Class II Biohazard Safety Hood." PCR preparation should occur in a separate room, within one of many PCR cabinets which are dedicated solely to PCR preparation. The PCR amplification should occur in thermocyclers located in an enclosed room. For post-amplification process of conventional PCR reactions, gel electrophoresis should be performed in yet another physically separate room. UV lights should be used in the PCR hoods and commercial solvents, such as DNAway (Molecular Bio Products, San Diego, Calif.), to decontaminate all work surfaces prior to and at the completion of any procedures occurring in that area. Sterile, disposable plasticware should be used wherever possible. All glassware should be autoclaved. All PCR reactions should be performed in individual closed tube systems as opposed to 96-well microtiter plates to eliminate cross contamination. Real-time PCR assays, for example, do not require gel electrophoresis and therefore eliminate post-amplification specimen handling. All technicians should only manipulate one specimen at a time. This means when a reagent is added to a batch of specimens, it occurs one tube at a time. The next patient's reaction tube is not opened until the previous patient's tube has been closed. Pipette tips used when dispensing reagents should be filtered to prevent aerosol contamination and are also replaced between all specimens. Reagents used during PCR preparation may be aliquoted into 1.5 ml microcentrifuge tubes, for example, as opposed to dispensation into stock bottles of greater volumes. This enables the laboratory to monitor potential contamination closely and discard any reagents, if ever necessary. The use of separate rooms is recommended to decontaminate an entire room if contamination is suspected. Positive and negative controls should be employed to assess false positives as well as false negatives. Uracil-N-glycosylase is recommended in every reaction to minimize, if not eliminate, any possible carry-over contamination.

Primers

Any pair of PCR primers may be employed in methods of the present invention that function to amplify target nucleic acids. The art of selection and synthesis of PCR primers in order to amplify a particular target sequence is indeed well-known to those of ordinary skill in the art. Typically, oligonucleotide primers are about 8 to about 50 nucleotides in length. Primers 12 to 24 nucleotides in length are preferred. Primer pairs that amplify particular nucleic acid molecules can be designed using, for example, a computer program such as OLIGO (Molecular Biology Insights, Inc., Cascade, Colo.). A biotin moiety, for example, is preferably attached to the 5' end of one of the primers to facilitate sample preparation for "pyrosequencing," a term which denotes the nucleotide sequencing method described in U.S. Pat. Nos. 6,210,891 and 6,258,568; Ronaghi et al., 1998, A sequencing method based on real-time pyrophosphate. Science 281:363-365; and Ronaghi, 2001, Pyrosequencing sheds light on DNA sequencing. Genome Research 11:3-11. Other entities, however, well known to those of skill in the art, may similarly be incorporated, integrated, or attached to one of the primers to facilitate the isolation of the resulting amplicon for pyrosequencing.

Real-Time PCR

Quantitative real-time PCR is a preferred method of amplification of a target nucleic acid. Products used to accomplish the methods are commercially available from several manufacturers including, but not limited, to Corbett Research (Mortlake, Australia), Cepheid (Sunnyvale, Calif.), BioRad (Hercules, Calif.), and Applied Biosystems (Foster City, Calif.). The Corbett Research (Melbourne, Australia) Rotor-Gene™ 3000, for example, is a centrifugal, real-time DNA amplification system.

Validation studies exemplified herein are merely a general demonstration of the utility and value of the present invention, namely a method for the collection and maintenance of detectability of a plurality of species of microbiological agents in a single gynecological sample, in the grand scheme of clinical diagnostics. The legitimacy of the PCR method is not a relevant factor, as its utility as an invaluable molecular biological tool has already been well established in the international scientific literature through the publication of thousands of peer-reviewed articles. Particularly, molecular amplification of nucleic acids by means of PCR is well-known to those of ordinary skill in the art, i.e., the ability of the PCR method to detect genetic sequences specific to a target pathogen within a given clinical specimen. The Applicants particularly highlight, however, that the methods described herein, which comprise providing transport media in a resealable container to a physician, clinical lab, or medical institution, with instructions for preparing and handling a gynecological sample, along with a test requisition form which indicates the detectability of a plurality of species described herein, affect the ability of a physician, for example, to collect a single swab sample of a gynecological environment for the maintenance of detectability of a plurality of species of microbiological agents. Example assays designed to test sensitivity, specificity, interference and optimization were performed to validate the operability of the methods and materials described herein, as claimed. In other words, PCR methods or reagents employed to detect microbiological agents are not relevant to the scope of the subject matter of the claims appended hereto. In contrast, the present invention is solely drawn toward methods and certain materials for collection and maintenance of detectability of a plurality of species of microbiological agents in a single gynecological swab sample.

Sensitivity refers to a method's ability to detect very minute amounts of a substance or organism. The frequency of a positive test result in patients who have the disease the test is designed to detect, is expressed mathematically as follows:

$$\text{Sensitivity} = \frac{\text{True Positives}}{\text{True Positives} + \text{False Negatives}} \times 100$$

Sensitivity studies were initially performed by purchasing well-characterized, validated organisms from the American Tissue Culture Collection (ATCC, Manassas, Va.). The DNA of the virus, bacteria, or fungi is then extracted and quantitated. Standards of known concentrations are used to determine the assay's ability to detect varying concentrations of genetic material. The extracted DNA is serially diluted to concentrations of 1:10, 1:100, 1:1,000 and 1:10,000. By evaluating the presence of bands in these dilutions of known concentrations, the sensitivity of a particular test can be established. For real-time PCR assays, the fluorescence acquisition profile generated from the amplification of the serial dilutions is analyzed. A region encompassing the genetic target of the assay is generally subcloned into a vector system. Through quantitation of the vector and the optimization of the assay as described infra, as few as 10 genomic equivalents of the pathogen can be reproducibly detected.

Specificity studies were used to assess the quality of the primer selection for the assay by determining if their organisms' DNA will cross-react in any way leading to false positives. Initially as a theoretical test, primers are cross-referenced against the billions of other genetic sequences which have been deposited in the public databases by international researchers and any potential conflicts are avoided. Next as an experimental confirmation, the primers and probes are assayed for their inability to amplify dozens of other known bacterial, viral, and fungal organisms which have been identified as human pathogens. An aliquot of the characterized positive control is also spiked in a suspension consisting of the DNA of numerous other organisms to ensure that the particular pathogen target genome is in no way masked or inhibited by other genomic sequences.

Interference studies are used to determine if other substances inherent to the specimen type will interfere with detection by PCR. Certain effects, such as masking the organism's target to produce a false negative, or cross-reactivity to produce a false positive are analyzed. Characteristics, such as the microcosm of normal flora of the genital tract, the abundance of various proteins found in blood, and natural inhibitors commonly found in other body fluids, such as urine, can all have detrimental effects on the PCR process, unless accounted for during the initial processing and extraction procedures.

Optimization studies are the final step of the validation process. In these assays, the concentrations of various reagents are varied such as template DNA, $MgCl_2$, and primers, and probes as well as the temperature and duration of each step of the thermocycling parameters to improve the clarity of bands or the intensity of signals, as well as eliminate streaks, multiple banding, or haziness, which can impede the visualization of the PCR products or interpretation of real-time PCR results. A method is preferred wherein a progress of at least one reaction is optically monitored by means of the system and/or wherein the presence or absence of a product of at least one reaction is optically determined and electronically recorded by the system.

Additional References

1. Adelson et al., 2005, Simultaneous detection of herpes simplex virus types 1 and 2 by real-time PCR and pyrosequencing. Journal of Clinical Virology 33:25-34. (manuscript published online on Nov. 14, 2004).
2. Trama et al., 2005, Detection of Candida species in vaginal samples in a clinical laboratory setting. Infectious Diseases in Obstetrics and Gynecology 13(2):63-67.
3. Trama et al., 2005, Detection and identification of Candida species associated with Candida vaginitis by real-time PCR and pyrosequencing. Molecular and Cellular Probes 19(2):145-152.
4. Trama et al. Analyzing Candida albicans gene mutations that contribute to azole resistance by pyrosequencing. American College of Obstetricians and Gynecologists 52nd Annual Clinical Meeting, May 1-5, 2004, Philadelphia, Pa.
5. Trama et al. Novel technique for identification of vulvovaginal candidiasis by real-time PCR and pyrosequencing. American College of Obstetricians and Gynecologists 52nd Annual Clinical Meeting, May 1-5, 2004, Philadelphia, Pa.
6. Adelson et al., Diagnosis of Neisseria gonorrhea, Chlamydia trachomatis, and Trichomonas vaginalis by real-time PCR. American College of Obstetricians and Gynecologists 52nd Annual Clinical Meeting, May 1-5, 2004, Philadelphia, Pa.
7. Mordechai et al., Prevalency of Candida species associated with Candida vaginitis in the United States. American Society of Microbiology 104th General Meeting, May 23-27, 2004, New Orleans, La., Poster C-108.
8. Adelson et al., Development of a real-time PCR assay for the simultaneous detection of herpes simplex virus types 1 and 2 with confirmation by pyrosequencing technology. American Society of Microbiology 104th General Meeting, May 23-27, 2004, New Orleans, La., Poster C-273.
9. Naurath et al., Detection and quantification of Gardnerella vaginalis by real-time PCR. American College of Obstetricians and Gynecologists 53rd Annual Clinical Meeting. May 7-11, 2005, San Francisco, Calif.
10. Trama et al, Detection of molluscum contagiosum virus by real-time PCR and pyrosequencing. American Society of Microbiology 105th General Meeting, Jun. 5-9, 2005, Atlanta, Ga.
11. Feola et al., Detection of Ureaplasma urealyticum, Mycoplasma hominis, and Mycoplasma genitalium by real-time PCR and pyrosequencing. American Society of Microbiology 105th General Meeting, Jun. 5-9, 2005, Atlanta, Ga.
12. Gygax et al., Erythromycin and clindamycin resistance in Group B Streptococcal clinical isolates. Presented by Dr. Martin E. Adelson at the 45th ICAAC (Interscience Conference on Antimicrobial Agents and Chemotherapy) Meeting in Washington DC on Dec. 16, 2005.
13. Adelson et al., Evaluation of UTM-RT for the molecular detection of a plurality of OB/GYN related pathogens. Presented by Dr. Martin E. Adelson at the 45th ICAAC (Interscience Conference on Antimicrobial Agents and Chemotherapy) Meeting in Washington DC on Dec. 17, 2005.

EXAMPLES

Example I

Validation Studies

To determine if Copan UTM-RT media is suitable for the molecular amplifications diagnostic testing, the following pathogens were purchased from ATCC and detection assays were performed:

TABLE 1

| | Pathogen | ATCC Catalogue Number |
|---|---|---|
| 1 | Bacteroides fragilis | 23745 |
| 2 | Candida albicans | 18804 |
| 3 | Candida glabrata | 2001 |
| 4 | Candida parapsilosis | 10233 |
| 5 | Candida tropicalis | 13803 |
| 6 | Chlamydia trachomatis | VR-901B |
| 7 | Gardnerella vaginalis | 14018 |
| 8 | Haemophilus ducreyi | 27721 |
| 9 | Herpes Simples Virus-1 | VR-1544 |
| 10 | Herpes Simples Virus-2 | VR-734 |
| 11 | Mobiluncus mulieris | 35243 |
| 12 | Mycoplasma hominis | 14027 |
| 13 | Neisseria gonorrhoeae | 27628 |
| 14 | Trichomonas vaginalis | 30246 |
| 15 | Ureaplasma urealyticum | 27618 |

Simulation of a Positive Clinical Specimen

Pathogens were purchased from ATCC in a lyophilized pellet form. Each pellet was dissolved in five ml of TE-buffer (10 mM Tris, pH 7.5, and 1 mM EDTA) in case of bacteria or yeast liquid media (10 g of yeast extract, 20 g of peptone dissolved in 1 L of distilled water, pH 7) in case of fungi. Virus cultures were purchased from ATCC as two ml liquid cultures. Dilutions were subsequently prepared as follows:

TABLE 2

| | Concentration (Designation) | | |
|---|---|---|---|
| | 1:1 (A) | 1:10 (B) | 1:100 (C) |
| Original Resuspension | 600 µl | 60 µl | 6 µl |
| TE Buffer (Bacteria, Virus) or Yeast Liquid Media (Fungi) | 0 µl | 540 µl | 594 µl |

DNA was extracted from 500 µl of A, B, and C dilutions using standard laboratory phenol/chloroform/ethanol precipitation protocols. For positive controls, pathogen-positive clinical specimens were identified from the initial laboratory diagnostic tests and 500 µl of the corresponding original cervical swab media specimen was extracted. Previously validated real-time PCRs for each set of pathogens was performed on DNA extracted from Dilutions A, B, and C as well as the clinical samples. Rotor-Gene software calculated $C_T$ values for the three ATCC dilutions and the clinical specimens (Rotor-Gene 3000 instrument). The $C_T$ values of the dilutions were compared with that obtained for the clinical specimens and a "simulated dilution" was extrapolated for the subsequent studies of the Copan UTM-RT transport medium. Based upon these studies, the following was selected:

TABLE 3

| | ATCC Resuspension | ATCC Resuspension used in this experiment | TE Buffer (Bacteria, Virus) or Yeast Liquid Media (Fungi) | Overall Dilution of pellet |
|---|---|---|---|---|
| Bacteria | 5 ml TE buffer added to pellet | 5 µl | 245 µl | 1:250 |
| Fungi | 5 ml TE buffer added to pellet | 5 µl | 245 µl | 1:250 |

TABLE 3-continued

| | ATCC Resuspension | ATCC Resuspension used in this experiment | TE Buffer (Bacteria, Virus) or Yeast Liquid Media (Fungi) | Overall Dilution of pellet |
|---|---|---|---|---|
| Viruses | 2 ml culture from ATCC | 2 µl | 198 µl | 1:100 |

The Applicants' studies suggest that spiking an ATCC culture (pellet suspended in 5 ml of medium or buffer) diluted at 1:50 simulates the concentration of bacterial and fungal pathogens (i.e., 250-fold dilution of ATCC culture) and 1:100 dilution simulates the viral pathogen (100-fold dilution of ATCC culture) in the clinical sample.

Studying the Stability of the Pathogen

For validation studies, Copan UTM-RT transport medium (Lot #A 303CS02) as provided by the manufacturer was pooled in a sterile bottle. Based upon the simulated dilutions described above for each pathogen, the following cocktails were prepared:

TABLE 4

| | | Per vial (A, B, & C) | |
|---|---|---|---|
| Cocktail | Pathogens | µl Pathogen* | µl Copan UTM-RT |
| 1 | Candida albicans | 80 µl | 3840 µl |
| | Neisseria gonorrhoeae | 80 µl | |
| 2 | Candida parapsilosis | 80 µl | 3800 µl |
| | Chlamydia trachomatis | 80 µl | |
| | Herpes Simplex Virus-1 | 40 µl | |
| 3 | Candida glabrata | 80 µl | 3800 µl |
| | Herpes Simplex Virus-2 | 40 µl | |
| | Trichomonas vaginalis | 80 µl | |
| 4 | Candida tropicalis | 80 µl | 3760 µl |
| | Mobiluncus mulieris | 80 µl | |
| | Ureaplasma urealyticum | 80 µl | |
| 5 | VBacteriodes fragilis | 80 µl | 3840 µl |
| | Mycoplasma hominis | 80 µl | |
| 6 | Gardnerella vaginalis | 80 µl | 3840 µl |
| | Haemophilis ducreyi | 80 µl | |

*Dilution prepared for each pathogen as detailed in Table 4.

Each cocktail was prepared in triplicate (15 ml tubes) and designated A, B, or C. Pathogen culture solution was added to obtain desired concentration which mimics the pathogen load in a positive clinical sample (1:250-fold dilution for ATCC bacterial and fungal culture and 1:100-fold dilution for ATCC virus culture). 500 µl of the above mix was transferred to three separate microcentrifuge tubes labeled Day 0 to 5.

Inoculated media vials of each cocktail were incubated at room temperature. At 24 hour intervals starting with Day 0 through Day 5, three microcentrifuge tubes were transferred to −20° C. storage. Aliquots from each vial were extracted for DNA by standard laboratory procedures after Day 5. Conventional and real-time PCR reactions for each pathogen on the appropriate cocktail followed. The summary of results is as follows:

TABLE 5

Figure 2:
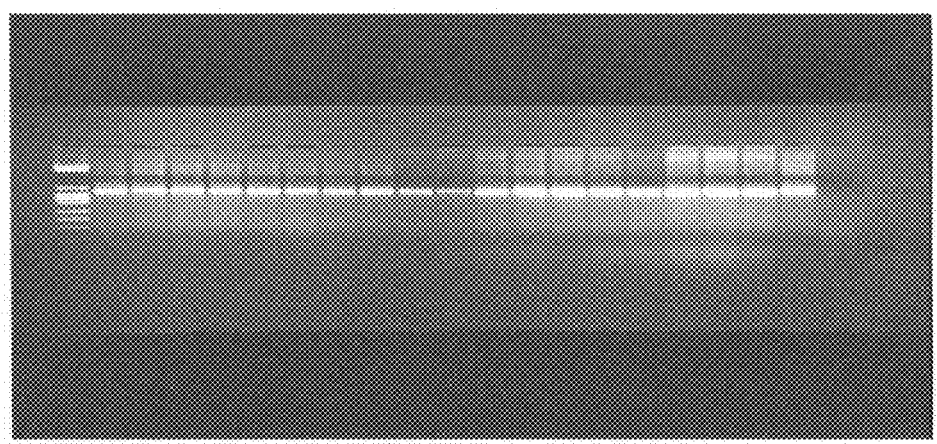
FIG. 2 displays validation data for *Bacteroides fragilis* wherein the PCR amplicon is 842 bp in which each sample was independently inoculated and extracted in triplicate. Lanes 2-4 represent detectability after storage at room temperature for zero days. Lanes 5-7 represent detectability after storage at room temperature for one day. Lanes 8-10 represent detectability after storage at room temperature for two days. Lanes 11-13 represent detectability after storage at room temperature for three days. Lanes 14-16 represent detectability after storage at room temperature for four days.

| | Pathogen | Type of PCR | # Positive Time Pts./ # Specimens Tested |
|---|---|---|---|
| 1 | Bacteriodes fragilis | Conventional PCR | 18/18 (see FIG. 2) |
| 2 | Candida albicans | Real-time PCR | 18/18 (see FIG. 4) |
| 3 | Candida glabrata | Real-time PCR | 14/18 (see FIG. 5) |
| 4 | Candida parapsilosis | Real-time PCR | 18/18 (see FIG. 6) |
| 5 | Candida tropicalis | Real-time PCR | 18/18 (see FIG. 7) |
| 6 | Chlamydia trachomatis | Real-time PCR | 18/18 (see FIG. 8) |
| 7 | Gardnerella vaginalis | Real-time PCR | 18/18 (see FIG. 9) |
| 8 | Haemophilis ducreyi | Real-time PCR | 18/18 (see FIG. 10) |
| 9 | Herpes Simplex Virus-1 | Real-time PCR | 18/18 (see FIG. 11) |
| 10 | Herpes Simplex Virus-2 | Real-time PCR | 18/18 (see FIG. 12) |
| 11 | Mobiluncus mulieris | Conventional PCR | 18/18 (see FIG. 3) |
| 12 | Mycoplasma hominis | Conventional PCR | 6/6 |
| 13 | Neisseria gonorrhoeae | Real-time PCR | 18/18 |
| 14 | Trichomonas vaginalis | Real-time PCR | 18/18 (see FIG. 13) |
| 15 | Ureaplasma urealyticum | Real-time PCR | 18/18 (see FIG. 14) |

Example II

DNA Extraction from Transport Media

For DNA extraction, see, e.g., Goessens et al., 1995, Influence of volume of sample processed on detection of Chlamydia trachomatis in urogenital samples by PCR. Journal of Clinical Microbiology 33:251-253.

The following steps outline the procedure to isolate and purify DNA from transport media. The specimen is submitted as a self-contained unit with transport media.

Proteinase K: 100 µl Tris (pH 7.5), 4.9 ml ddH$_2$O, 5 ml Glycerol. Dissolve well and store at −20° C. as 500 µl aliquots.

10% SDS: 10 g SDS in 100 ml of ddH$_2$O.

Equipment:
  Disposable pipette tips
  Disposable transfer pipette
  Laboratory timer
  1.5 ml microcentrifuge tube
  55° C. water bath
  Pipettes to deliver a range of 1-1000 µl Procedure:
  1. Mix the swab thoroughly in the transport media.
  2. Pipette 470 µl of transport media into a labeled microcentrifuge tube.
  3. Add 25 µl of 10% SDS and 12 µl of Proteinase K. Mix well.
  4. Incubate for 2 hours in 55° C. water bath.
  5. After 2 hours, place 200 µl of Tris saturated phenol and 200 µl of chloroform:isoamyl alcohol (24:1) in the tube. Shake the tube to mix the layers.
  6. Centrifuge at 14,000 rpm for 5 minutes at room temperature. This will separate the layers.
  7. Remove the top chloroform layer (containing the DNA) being careful not to pipette any of the bottom or middle layers. Place this into another labeled microcentrifuge tube. The first tube containing the remaining layers may be discarded.
  8. To this new tube add 0.1× volume of 3 M sodium acetate. Also add 2× volumes of cold 100% ethanol. Vortex and place in −20° C. overnight.
  9. Centrifuge the tube at 14,000 rpm at 4° C. for 10 minutes. This will pellet the precipitated DNA.
  10. Remove and discard the supernatant. Add 1000 µl of 70% ethanol to wash the pellet. Slightly resuspend the pellet.

11. Centrifuge the tube again at 14,000 rpm at 4° C. for 5 minutes to form a pellet.

12. Place the tube with the top open into the CentriVap (Labconco, Kansas City, Mo.). Spin at 35° C. for approximately 15 minutes. Spin until the pellet is dry, being very careful not to overdry.

13. Resuspend the pellet in 20 µl of ddH$_2$O.

14. Quantitate the DNA using a spectrophotometer.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

The invention claimed is:

1. A method for the collection and maintenance of detectability of a plurality of species of microbiological agents selected from the group consisting of bacteria, fungi, and viruses, in a primary gynecological sample and for handling a plurality of primary gynecological samples and managing information associated therewith for reporting a sum of diagnostic results for each primary gynecological sample, comprising the steps of:
  (a) collecting a primary gynecological sample from a patient,
  (b) providing a transport medium in a resealable container with instructions for preparation and handling of said primary gynecological sample and an indication of the detectability of the plurality of species contained in said primary gynecological sample,
    wherein said transport medium comprises bovine serum albumin, L-cysteine, gelatin, sucrose, L-glutamic acid, vancomycin, amphotericin B and colistin;
  (c) adding said primary gynecological sample to said transport medium, wherein said transport medium supports viability of said plurality of species of microbiological agents sustained at room temperature for at least 48 hours and up to 5 days;
  (d) receiving a plurality of said primary gynecological samples in step (c), each primary gynecological sample having an identity and a test requisition form containing information associated therewith,
    wherein said information indicates a test for at least one species from a plurality of species;
  (e) entering said information into a system to create a requisition file for each primary gynecological sample;
  (f) processing said information to create a list of each primary gynecological sample to be tested for each species;
  (g) dispensing an aliquot corresponding to each primary gynecological sample into an individual vessel, to create a secondary gynecological sample, for each designated test for different species on each secondary gynecological sample;
  (h) assembling a general supply of master reagent mix for each different test;
  (i) combining an aliquot of master reagent mix for each test with each corresponding secondary gynecological sample to produce a diagnostic test reaction for each secondary gynecological sample;
  (j) determining the presence or absence of a certain product of each reaction to produce a result, recording said result of each reaction;
  (k) combining said result of each reaction derived from each primary gynecological sample into the requisition file for each primary gynecological sample on the system, thereby producing a sum of results for each primary gynecological sample; and
  (l) reporting said sum of results to an attending physician who ordered the test within 24-48 hours after receipt of said primary gynecological sample in sample (d).

2. The method according to claim 1 wherein at least one species within the plurality of species is indicative of at least one gynecological disorder.

3. The method according to claim 1 wherein the plurality of species comprise *Chlamydia trachomatis* and *Neisseria gonorrhoeae*.

4. The method according to claim 1 wherein the plurality of species comprise *Gardnerella vaginalis, Mobiluncus mulieris, Mobiluncus curtisii*, and *Bacteroides fragilis*.

5. The method according to claim 1 wherein the plurality of species comprise *Candida albicans, Candida glabrata, Candida parapsilosis*, and *Candida tropicalis*.

6. The method according to claim 1 wherein the plurality of species comprise *Mycoplasma genitalium, Mycoplasma hominis*, and *Ureaplasma urealyticum*.

7. The method according to claim 1 wherein the plurality of species comprise Herpes simplex virus, *Treponema pallidum*, and *Haemophilis ducreyi*.

8. The method according to claim 1 wherein at least one (1) species of the plurality of species is selected from the group consisting of *Gardnerella vaginalis, Molluscum contagiosum* Virus, *Mycoplasma genitalium*, and *Mycoplasma hominis*.

9. The method according to claim 1 wherein the plurality of species comprise at least one species selected from the group consisting of *Molluscum contagiosum* virus, *Mycoplasma genitalium, Mycoplasma hominis, Candida dubliniensis, Candida krusei, Candida lusitaneae, Atopobium vaginae*, erythromycin-resistant *Streptococcus agalactiae*, clindamycin-resistant *Streptococcus agalactiae, Lymphogranuloma venereum*, HPV-16, HPV-18, HPV-31, HPV-33, HPV-35, HPV-39, HPV-45, HPV-51, HPV-52, HPV-56, HPV-58, HPV-59, HPV-66, HPV-68, HPV-6/11, HPV-42, HPV-43 and HPV-44.

10. A method for the collection and maintenance of detectability of a plurality of species of microbiological agents selected from the group consisting of bacteria, fungi, and viruses, in a primary gynecological sample and for handling a plurality of primary gynecological samples and managing information associated therewith for reporting a sum of diagnostic results for each primary gynecological sample, comprising the steps of:
  (a) providing a kit comprised of a transport medium in a resealable container, a sterile swab, and instructions for preparation and handling of a primary gynecological sample and a writing which indicates the detectability of the plurality of species,
    wherein said transport medium comprises bovine serum albumin, L-cysteine, gelatin, sucrose, L-glutamic acid, vancomycin, amphotericin B, and colistin, and
    wherein viability of said plurality of species of microbiological agents is sustained at room temperature for at least 48 hours and up to 5 days;
  (b) adding a collected primary gynecological sample to said transport medium in said kit, wherein said transport medium supports viability of said plurality of species of microbiological agents sustained at room temperature for at least 48 hours and up to 5 days;

(c) receiving a plurality of said primary gynecological sample in said transport medium, each such sample being derived from a kit as recited in (a), having an identity and a test requisition form containing information associated therewith, wherein said test requisition information indicates a test for at least one species from the plurality of species;

(d) entering said information into a system to create a requisition file for each primary gynecological sample;

(e) processing said information to create a list of primary gynecological samples to be tested for each species;

(f) dispensing an aliquot corresponding to each primary gynecological sample into an individual vessel, to create a secondary gynecological sample, for each designated test for different species on each gynecological sample;

(g) assembling a general supply of master reagent mix for each different test;

(h) combining an aliquot of master reagent mix for each test with each corresponding secondary gynecological sample to produce a diagnostic test reaction for each secondary gynecological sample;

(i) determining the presence or absence of a certain product of each reaction to produce a result, recording the result of each reaction;

(j) combining the result of each reaction derived from each primary gynecological sample into the requisition file for each gynecological sample on the system, thereby producing a sum of results for each primary gynecological sample; and (k) -reporting the results to an attending physician who ordered the test within 24-48 hours after receipt of said primary gynecological sample in step (c), wherein the plurality of species comprises at least one species selected from the group consisting of *Molluscum contagiosum* virus, *Mycoplasma genitalium*, *Mycoplasma hominis*, *Candida dubliniensis*, *Candida krusei*, *Candida lusitaneae*, *Atopobium vaginae*, erythromycin-resistant *Streptococcus agalactiae*, clindamycin-resistant *Streptococcus agalactiae*, *Lymphogranuloma venereum*, HPV-16, HPV-18, HPV-31, HPV-33, HPV-35, HPV-39, HPV-45, HPV-51, HPV-52, HPV-56, HPV-58, HPV-59, HPV-66, HPV-68, HPV-6/11, HPV-42, HPV-43, and HPV-44.

11. The method according to claim 10 wherein the presence or absence of a product of at least one reaction is electronically recorded by means of the system.

12. The method according to claim 11 wherein at least one diagnostic test reaction comprises a real-time Polymerase Chain Reaction (PCR).

13. The method according to claim 10 wherein the results are reported within about twenty four (24) hours of receiving the sample.

14. The method according to claim 10 wherein the results are reported within about thirty (30) hours of receiving the sample.

15. The method according to claim 10 which comprises pyrosequencing.

16. A method for the collection and maintenance of detectability of a plurality of species of microbiological agents of bacteria, in a primary gynecological sample and for handling a plurality of primary gynecological samples and managing information associated therewith for reporting a sum of diagnostic results for each primary gynecological sample, comprising the steps of:

(a) providing a transport medium in a resealable container with instructions for preparation and handling of a primary gynecological sample and an indication of the detectability of the plurality of species, wherein said transport medium comprises bovine serum albumin, L-cysteine, gelatin, sucrose, L-glutamic acid, vancomycin, amphotericin B, and colistin, and wherein viability of said plurality of species of microbiological agents is sustained at room temperature for at least 48 hours and up to 5 days;

(b) receiving a plurality of said primary gynecological samples, each primary gynecological sample having an identity and a test requisition form containing information associated therewith, wherein the test requisition information indicates a test for at least one species from a plurality of species;

(c) entering the information into a system to create a requisition file for each primary gynecological sample;

(d) processing the information to create a list of each primary gynecological samples to be tested for each species;

(e) dispensing an aliquot corresponding to each primary gynecological sample into an individual vessel, to create a secondary gynecological sample, for each designated test for different species on each secondary gynecological sample;

(f) assembling a general supply of master reagent mix for each different test;

(g) combining an aliquot of master reagent mix for each test with each corresponding secondary gynecological sample to produce a diagnostic test reaction for each secondary gynecological sample;

(h) determining the presence or absence of a certain product of each reaction to produce a result, recording the result of each reaction;

(i) combining the result of each reaction derived from each primary gynecological sample into the requisition file for each primary gynecological sample on the system, thereby producing a sum of results for each primary gynecological sample; and (j) reporting the results to an attending physician who ordered the test within 24-48 hours after receipt of said primary gynecological sample in step (b), wherein the plurality of species comprises at least one species selected from the group consisting of *Atopobium vaginae*, erythromycin-resistant *Streptococcus agalactiae*, clindamycin-resistant *Streptococcus agalactiae*.

* * * * *